US011123005B2

(12) United States Patent
Sarkar et al.

(10) Patent No.: US 11,123,005 B2
(45) Date of Patent: Sep. 21, 2021

(54) METHOD AND APPARATUS FOR ATRIAL TACHYARRHYTHMIA DETECTION

(71) Applicant: Medtronic, Inc., Minneapolis, MN (US)

(72) Inventors: Shantanu Sarkar, Roseville, MN (US); Wade M. Demmer, Coon Rapids, MN (US); Todd J. Sheldon, North Oaks, MN (US); Vincent E. Splett, Apple Valley, MN (US)

(73) Assignee: Medtronic, Inc, Minneapolis, MN (US)

( * ) Notice: Subject to any disclaimer, the term of this patent is extended or adjusted under 35 U.S.C. 154(b) by 118 days.

(21) Appl. No.: 16/186,937

(22) Filed: Nov. 12, 2018

(65) Prior Publication Data

US 2020/0146580 A1 May 14, 2020

(51) Int. Cl.
*A61B 5/0464* (2006.01)
*A61B 5/363* (2021.01)
*A61B 5/00* (2006.01)
*A61N 1/362* (2006.01)
*A61N 1/39* (2006.01)
*A61B 5/361* (2021.01)
*A61B 5/287* (2021.01)
*A61B 5/316* (2021.01)
*A61B 5/352* (2021.01)

(52) U.S. Cl.
CPC .............. *A61B 5/363* (2021.01); *A61B 5/361* (2021.01); *A61B 5/686* (2013.01); *A61N 1/3622* (2013.01); *A61N 1/3956* (2013.01); *A61B 5/0031* (2013.01); *A61B 5/287* (2021.01); *A61B 5/316* (2021.01); *A61B 5/352* (2021.01); *A61B 5/7264* (2013.01); *A61N 1/3624* (2013.01)

(58) Field of Classification Search
CPC .................................................... A61B 5/686
See application file for complete search history.

(56) References Cited

U.S. PATENT DOCUMENTS

| | | | |
|---|---|---|---|
| 4,485,813 A | 12/1984 | Anderson et al. |
| 5,052,388 A | 10/1991 | Sivula et al. |
| 5,480,412 A | 1/1996 | Mouchawar et al. |
| 5,507,782 A | 4/1996 | Kieval et al. |
| 5,593,431 A | 1/1997 | Sheldon |
| 5,693,432 A | 12/1997 | Matsumoto |
| 5,885,471 A | 3/1999 | Ruben et al. |
| 6,044,297 A | 3/2000 | Sheldon et al. |
| 7,031,765 B2 | 4/2006 | Ritscher et al. |
| 7,130,681 B2 | 10/2006 | Gebhardt et al. |
| 7,537,569 B2 | 5/2009 | Sarkar et al. |

(Continued)

OTHER PUBLICATIONS (PCT/US2019/060731) PCT Notification of Transmittal of the International Search Report and the Written Opinion of the International Searching Authority, dated May 12, 2020, 9 pages.

*Primary Examiner* — Rex R Holmes
*Assistant Examiner* — Jennifer L Ghand

(57) ABSTRACT

An implantable medical device is configured to determine a first atrial arrhythmia score from ventricular events sensed by a sensing circuit of an implantable medical device and determine a second atrial arrhythmia score from an intraventricular signal comprising atrial mechanical event signals attendant to atrial systole and produced by a sensor of the implantable medical device. An atrial arrhythmia is detected based on the first atrial arrhythmia score and the second atrial arrhythmia score.

33 Claims, 11 Drawing Sheets

(56) References Cited

U.S. PATENT DOCUMENTS

| | | |
|---|---|---|
| 7,623,911 B2 | 11/2009 | Sarkar et al. |
| 7,627,368 B2 | 12/2009 | Houben et al. |
| 8,433,409 B2 | 4/2013 | Johnson et al. |
| 8,532,785 B1 | 9/2013 | Crutchfield et al. |
| 8,541,131 B2 | 9/2013 | Lund et al. |
| 8,639,316 B2 | 1/2014 | Sarkar |
| 8,639,328 B2 | 1/2014 | Hettrick et al. |
| 8,977,350 B2 | 3/2015 | Sarkar et al. |
| 9,399,140 B2 | 7/2016 | Cho et al. |
| 9,486,155 B2 | 11/2016 | Sarkar et al. |
| 9,603,543 B2 | 3/2017 | Sarkar et al. |
| 9,675,269 B2 | 6/2017 | Sarkar et al. |
| 9,775,872 B2 | 10/2017 | Banov |
| 9,775,982 B2 | 10/2017 | Grubac et al. |
| 9,936,890 B2 | 4/2018 | Sarkar et al. |
| 9,962,102 B2 | 5/2018 | Sarkar et al. |
| 2011/0160787 A1 | 6/2011 | Greenhut et al. |
| 2012/0095521 A1 | 4/2012 | Hintz |
| 2012/0238891 A1 | 9/2012 | Sarkar et al. |
| 2016/0023000 A1 | 1/2016 | Cho et al. |
| 2016/0213270 A1* | 7/2016 | Cao ........................ A61B 5/046 |
| 2017/0119273 A1* | 5/2017 | Thakur ................. A61B 5/046 |
| 2017/0281034 A1 | 10/2017 | Higgins et al. |
| 2018/0028086 A1 | 2/2018 | Cao et al. |
| 2018/0085588 A1 | 3/2018 | Splett et al. |
| 2018/0085589 A1 | 3/2018 | Splett et al. |
| 2018/0117337 A1 | 5/2018 | Demmer et al. |
| 2018/0154154 A1 | 6/2018 | Sheldon et al. |

\* cited by examiner

METHOD AND APPARATUS FOR ATRIAL TACHYARRHYTHMIA DETECTION

TECHNICAL FIELD

This disclosure relates to an implantable medical device and method for detecting atrial tachyarrhythmia using an intraventricular sensor signal including atrial mechanical event signals.

BACKGROUND

Implantable cardiac pacemakers are often placed in a subcutaneous pocket and coupled to one or more transvenous medical electrical leads carrying pacing and sensing electrodes positioned in the heart. A cardiac pacemaker implanted subcutaneously may be a single chamber pacemaker coupled to one transvenous medical lead for positioning electrodes in one heart chamber, atrial or ventricular, or a dual chamber pacemaker coupled to two intracardiac leads for positioning electrodes in both an atrial and a ventricular chamber. Multi-chamber pacemakers are also available that may be coupled to three leads, for example, for positioning electrodes for pacing and sensing in one atrial chamber and both the right and left ventricles.

Intracardiac pacemakers have recently been introduced that are implantable within a ventricular chamber of a patient's heart for delivering ventricular pacing pulses. Such a pacemaker may sense R-wave signals attendant to intrinsic ventricular depolarizations and deliver ventricular pacing pulses in the absence of sensed R-waves. While single chamber ventricular sensing and pacing by an intracardiac ventricular pacemaker may adequately address some cardiac conditions, some patients may benefit from atrial and ventricular (dual chamber) sensing for providing atrial-synchronized ventricular pacing and maintaining a more normal heart rhythm.

Some patients having a pacemaker may experience tachyarrhythmia, which may originate in the ventricular chambers, e.g., ventricular tachycardia (VT) or ventricular fibrillation (VF). A fast ventricular rate, however, may originate in and be conducted from the atrial chambers to the ventricles in patients with intact atrioventricular conduction. An atrial tachyarrhythmia that originates in the upper heart chambers and is conducted to the ventricles is sometimes referred to as supraventricular tachyarrhythmia (SVT). Anti-tachycardia pacing therapy (ATP) and/or a cardioversion shock may be delivered to the ventricles to treat VT or VF but is likely ineffective in terminating an SVT. As such, discrimination of SVT from VT and VF enables proper diagnosis and treatment of a heart rhythm condition.

SUMMARY

The techniques of this disclosure generally relate to an implantable medical device configured to detect atrial tachyarrhythmia. An implantable medical device operating according to the techniques disclosed herein may be implanted in the ventricle of a patient's heart. The device has a sensor configured to produce an intraventricular signal that includes mechanical atrial systolic event signals. In some examples, the sensor is a motion sensor, e.g., an accelerometer, configured to produce an intraventricular motion signal. The medical device may be an intracardiac ventricular pacemaker configured to sense atrial mechanical events attendant atrial systole from the motion signal and sense ventricular events from a cardiac electrical signal and/or the motion signal for use in determining ventricular cycle lengths (VCLs). The pacemaker may detect atrial tachyarrhythmia based on an analysis of VCL irregularity and atrial mechanical event evidence determined from the intraventricular signal. In some examples, detection of atrial mechanical events from an intraventricular motion signal during irregular VCLs may be used to determine an atrial event evidence score that may be used to reduce the likelihood of detecting atrial fibrillation by the implantable medical device.

In one example, the disclosure provides an implantable medical device including a sensor configured to produce an intraventricular signal including an atrial mechanical event signal attendant to atrial mechanical systole, a sensing circuit configured to sense ventricular events sensed by the sensing circuit, a memory configured to store atrial arrhythmia episode data, and a control circuit coupled to the sensor, the sensing circuit, and the memory. The control circuit may be configured to determine a first atrial arrhythmia score from the sensed ventricular events. The atrial arrhythmia score is correlated to a presence of atrial arrhythmia. The control circuit is further configured to determine a second atrial arrhythmia score from the intraventricular signal based on the atrial mechanical event signals, and detect an atrial arrhythmia based on the first atrial arrhythmia score and the second atrial arrhythmia score. The control circuit may generate an atrial arrhythmia detection notification in response to detecting the atrial arrhythmia. In some examples, the control circuit updates the atrial arrhythmia episode data stored in the memory including an indication of the atrial arrhythmia detection. The implantable medical device may include a telemetry circuit configured to transmit the updated atrial arrhythmia episode data. The updated atrial arrhythmia episode data may be transmitted to an external device for generating a display of the updated atrial arrhythmia episode data. In some examples, the implantable medical device includes a pulse generator configured to adjust or withhold a pacing therapy in response to the control circuit detecting the atrial arrhythmia.

In another example, the disclosure provides a method including determining a first atrial arrhythmia score from ventricular events sensed by a sensing circuit of an implantable medical device. The first atrial arrhythmia score is correlated to a presence of atrial arrhythmia. The method further includes determining a second atrial arrhythmia score from an intraventricular signal produced by a sensor of the implantable medical device. The intraventricular signal includes an atrial mechanical event signal attendant to atrial systole. The second atrial arrhythmia score is based on the atrial mechanical event signals. The method includes detecting an atrial arrhythmia based on the first atrial arrhythmia score and the second atrial arrhythmia score and updating atrial arrhythmia episode data stored in a memory of the implantable medical device in response to detecting the atrial arrhythmia. The update includes an indication of the detected atrial arrhythmia. The method may include transmitting the updated atrial arrhythmia episode data. In some examples, the updated atrial arrhythmia episode data is transmitted to an external device for generating a display of the atrial arrhythmia episode data. In some examples, the method includes adjusting or withholding a ventricular pacing therapy generated by a pulse generator of the implantable medical device in response to detecting the atrial arrhythmia.

In another example, the disclosure provides a non-transitory, computer-readable storage medium comprising a set of instructions which, when executed by a control circuit of an implantable medical device, cause the device to determine a first atrial arrhythmia score from ventricular events sensed by a sensing circuit of the implantable medical device and determine a second atrial arrhythmia score from an intraventricular signal produced by a sensor of the implantable medical device. The first atrial arrhythmia score is correlated to a presence of atrial arrhythmia. The intraventricular signal includes an atrial mechanical event signal attendant to atrial systole. The second atrial arrhythmia score is based on the atrial mechanical event signals. The instructions further cause the implantable medical device to detect an atrial arrhythmia based on the first atrial arrhythmia score and the second atrial arrhythmia score and update atrial arrhythmia episode data stored in a memory of the implantable medical device in response to detecting the atrial arrhythmia. The instructions may cause the device to transmit the atrial arrhythmia episode data in response to the updating, including an indication of the detected atrial arrhythmia. In some examples the updated atrial arrhythmia episode data is transmitted to an external device for generating a display of the atrial arrhythmia episode data. The instructions may cause a pulse generator of the implantable medical device to adjust or withhold a ventricular pacing therapy in response to detecting the atrial arrhythmia.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

In general, this disclosure describes techniques for detecting atrial tachyarrhythmia by an implantable medical device. In various examples, the implantable medical device is an intracardiac pacemaker wholly implantable in a ventricular chamber. P-waves, attendant to atrial depolarizations, are generally difficult to sense reliably from the cardiac electrical signal received by an intracardiac ventricular pacemaker. P-wave sensing may not be practical for detecting and discriminating atrial tachyarrhythmias from ventricular tachyarrhythmias by an intracardiac ventricular pacemaker. Yet the detection and discrimination of atrial and ventricular tachyarrhythmias is important information that clinicians have grown to expect to receive from implantable pacemakers that have have both atrial and ventricular electrodes in place in the atrial and ventricular heart chambers, respectively, for sensing atrial and ventricular electrical signals. Detecting and discriminating atrial and ventricular arrhythmias may also be used by an implantable pacemaker in properly controlling therapy delivery.

Using techniques disclosed herein, a single chamber, intracardiac ventricular pacemaker is configured to detect atrial tachyarrhythmia based on an analysis of ventricular events in combination with an analysis of atrial mechanical events sensed from an intraventricular signal. As described below, atrial mechanical events attendant to atrial mechanical systole are sensed from an intraventricular signal produced by a sensor included in the pacemaker implantable within a ventricular chamber of the heart. For example, a motion signal produced by an accelerometer includes an atrial systolic event signal corresponding to atrial mechanical contraction and the active filling phase of the ventricle, sometimes referred to as the "atrial kick." A sensor signal acquired from within a ventricular chamber is referred to herein as an "intraventricular signal." An intracardiac ventricular pacemaker may receive a cardiac electrical signal for sensing R-waves attendant to the depolarization of the ventricular myocardium for determining evidence of atrial arrhythmia. For example, irregularity of VCLs is a positive indicator for atrial fibrillation (AF). As disclosed herein, an intracardiac ventricular pacemaker may be configured to use evidence of one or more atrial systolic mechanical events sensed from an intraventricular signal for reducing the likelihood of detecting atrial fibrillation based on evidence of VCL irregularity.

Figure 1:
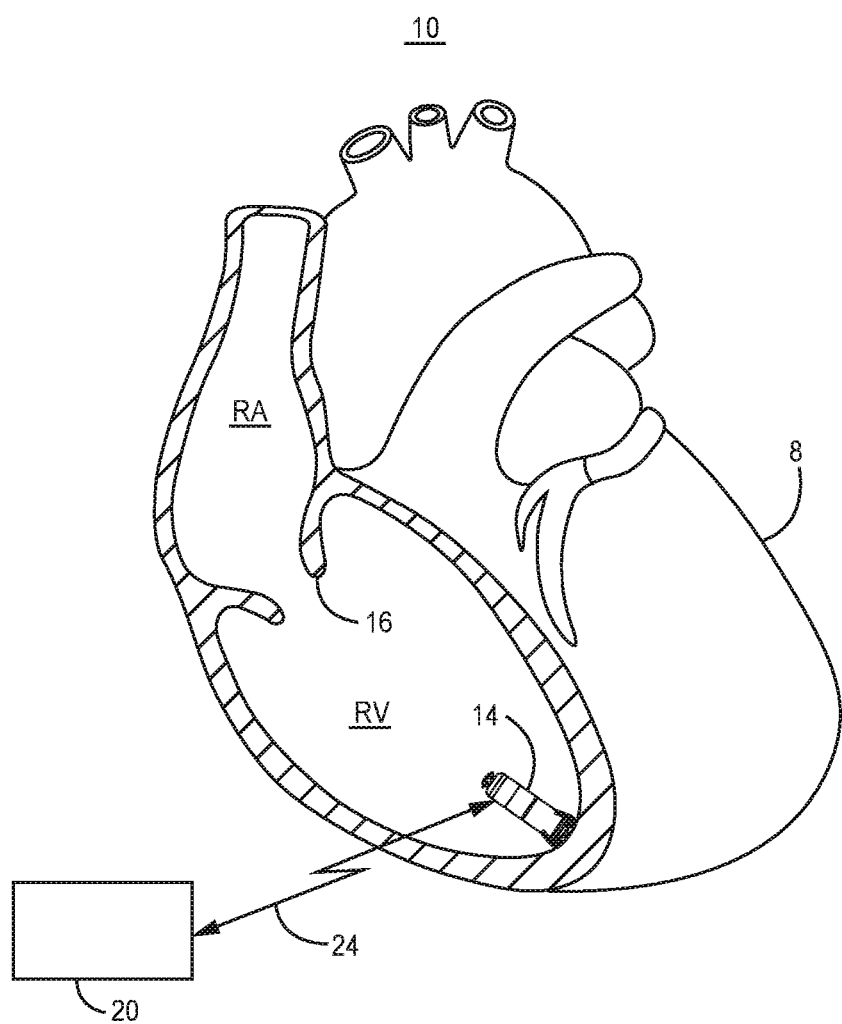
FIG. 1 is a conceptual diagram illustrating an intracardiac pacing system that may be used to detect atrial tachyarrhythmia according to the techniques disclosed herein.

FIG. 1 is a conceptual diagram illustrating an intracardiac pacing system 10 that may be used to sense cardiac electrical signals and motion signals induced by cardiac motion and flowing blood and provide pacing therapy to a patient's heart 8. System 10 includes a ventricular intracardiac pacemaker 14, which may be capable of wireless communication with an external device 20. Pacemaker 14 may be a transcatheter intracardiac pacemaker which is adapted for implantation wholly within a heart chamber, e.g., wholly within the right ventricle (RV) or wholly within the left ventricle (LV) of heart 8 for sensing cardiac signals and delivering ventricular pacing pulses. Pacemaker 14 may be reduced in size compared to subcutaneously implanted pacemakers and may be generally cylindrical in shape to enable transvenous implantation via a delivery catheter.

Pacemaker 14 is shown positioned in the RV, along an endocardial wall, e.g., near the RV apex though other locations are possible. The techniques disclosed herein are not limited to the pacemaker location shown in the example of FIG. 1 and other positions within heart 8 are possible. For example, ventricular intracardiac pacemaker 14 may be positioned in the LV and configured to detect cardiac motion signals and determine ventricular cycle lengths for detecting atrial tachyarrhythmia using the techniques disclosed herein. Pacemaker 14 may be positioned within the RV or LV to provide respective right ventricular or left ventricular pacing, sensing cardiac electrical signals and sensing cardiac motion signals by a motion sensor within the ventricular chamber.

Pacemaker 14 is capable of producing electrical stimulation pulses, e.g., pacing pulses, delivered to heart 8 via one or more electrodes on the outer housing of the pacemaker. For example, in the position shown, pacemaker 14 is configured to deliver RV pacing pulses and sense an RV cardiac electrical signal using housing based electrodes for producing an RV electrogram (EGM) signal. The cardiac electrical signals may be sensed using the housing-based electrodes that are also used to deliver pacing pulses to the RV.

Pacemaker 14 may be configured to control ventricular pacing in a manner that promotes synchrony between atrial activation and ventricular activation, e.g., by maintaining a target atrioventricular (AV) interval between atrial and ventricular pacing pulses delivered by pacemaker 14. That is, pacemaker 14 controls ventricular pacing pulse delivery to maintain a desired AV interval between atrial contractions corresponding to atrial systole and ventricular pacing pulses delivered to cause ventricular depolarization followed by ventricular contraction, corresponding to ventricular systole. At times, pacemaker 14 may be configured to control the delivery of ventricular pacing pulses to the RV to maintain a desired minimum ventricular rate, e.g., in a VVI or VVIR pacing mode, that is asynchronous with atrial events. The minimum ventricular rate may be a programmed lower rate, e.g., 40 to 60 pulses per minute, or a temporary lower rate set based on patient activity as an indication of metabolic demand. Pacemaker 14 may use the motion signal from the motion sensor to determine a patient activity metric for controlling the ventricular pacing rate to meet the patient's metabolic demand, as indicated by the patient activity metric.

Atrial systolic events producing the active ventricular filling phase are detected by pacemaker 14 from a motion sensor such as an accelerometer enclosed by the housing of pacemaker 14. The motion signal produced by an accelerometer implanted within a ventricular chamber includes motion signals caused by ventricular and atrial events. For example, acceleration of blood flowing into the RV through the tricuspid valve 16 between the RA and RV caused by atrial systole, or the "atrial kick," may be detected by pacemaker 14 from the signal produced by an accelerometer included in pacemaker 14. Other cardiac signals that may be detected by pacemaker 14 from an intraventricular motion signal, such as cardiac motion signals caused by ventricular contraction and relaxation, are described below, e.g., in conjunction with FIG. 4.

Atrial P-waves that are attendant to atrial depolarization are relatively low amplitude signals in the near-field ventricular cardiac electrical signal received by pacemaker 14 (e.g., compared to the near-field R-wave) and therefore can be difficult to reliably detect from the cardiac electrical signal acquired by pacemaker 14 implanted in a ventricular chamber. Detecting an atrial rhythm for tachyarrhythmia monitoring and/or atrial-synchronized ventricular pacing by pacemaker 14 may not be reliable when based solely on a cardiac electrical signal received by pacemaker 14. According to the techniques disclosed herein, pacemaker 14 includes a motion sensor, such as an accelerometer, and is configured to detect an atrial event corresponding to atrial mechanical activation, or atrial systole, from a signal produced by the motion sensor. Ventricular pacing pulses may be synchronized to the atrial event that is detected from the motion sensor signal by setting a programmable AV pacing interval that controls the timing of the ventricular pacing pulse relative to the detected atrial systolic event. As described below, atrial event detection from the motion signal may be used for detecting atrial tachyarrhythmia that is additionally based on an analysis of VCLs determined as the time intervals between successive ventricular events, e.g., sense R-waves.

Pacemaker 14 may be capable of bidirectional wireless communication with an external device 20 for programming cardiac electrical signal sensing and pacing control parameters as well as mechanical event (motion signal) sensing parameters, which may be utilized for detecting ventricular mechanical events and the atrial systolic event from the motion sensor signal. Aspects of external device 20 may generally correspond to the external programming/monitoring unit disclosed in U.S. Pat. No. 5,507,782 (Kieval, et al.), hereby incorporated herein by reference in its entirety. External device 20 is often referred to as a "programmer" because it is typically used by a physician, technician, nurse, clinician or other qualified user for programming operating parameters in pacemaker 14. External device 20 may be located in a clinic, hospital or other medical facility. External device 20 may alternatively be embodied as a home monitor or a handheld device that may be used in a medical facility, in the patient's home, or another location. Operating parameters, including sensing and therapy delivery control parameters, may be programmed into pacemaker 14 using external device 20.

External device 20 is configured for bidirectional communication with implantable telemetry circuitry included in pacemaker 14. External device 20 establishes a wireless communication link 24 with pacemaker 14. Communication link 24 may be established using a radio frequency (RF) link such as BLUETOOTH®, Wi-Fi, Medical Implant Communication Service (MICS) or other communication bandwidth. In some examples, external device 20 may include a programming head that is placed proximate pacemaker 14 to establish and maintain a communication link 24, and in other examples external device 20 and pacemaker 14 may be configured to communicate using a distance telemetry and circuitry that does not require the use of a programming head and does not require user intervention to maintain a communication link. An example RF telemetry communication system that may be implemented in system 10 is generally disclosed in U.S. Pat. No. 5,683,432 (Goedeke, et al.), hereby incorporated herein by reference in its entirety. External device 20 may display data and information relating to pacemaker functions to a user for reviewing pacemaker operation and programmed parameters as well as EGM signals transmitted from pacemaker 14, motion sensor signals acquired by pacemaker 14, or other physiological data that is acquired by and retrieved from pacemaker 14 during an interrogation session. Data transmitted to external device 20 from pacemaker 14 may include the motion sensor signal, the cardiac electrical signal, and/or a marker channel indicating the timing and intervals of events sensed from the motion sensor signal and/or an episode of the cardiac electrical signal associated with a tachyarrhythmia detection.

It is contemplated that external device 20 may be in wired or wireless connection to a communications network via a telemetry circuit that includes a transceiver and antenna or via a hardwired communication line for transferring data to a centralized database or computer to allow remote management of the patient. Remote patient management systems including a centralized patient database may be configured to utilize the presently disclosed techniques to enable a clinician to review EGM, motion sensor signal, and marker channel data and authorize programming of sensing and therapy control parameters in pacemaker 14, e.g., after viewing a visual representation of EGM, motion sensor signal and marker channel data.

Figure 2:
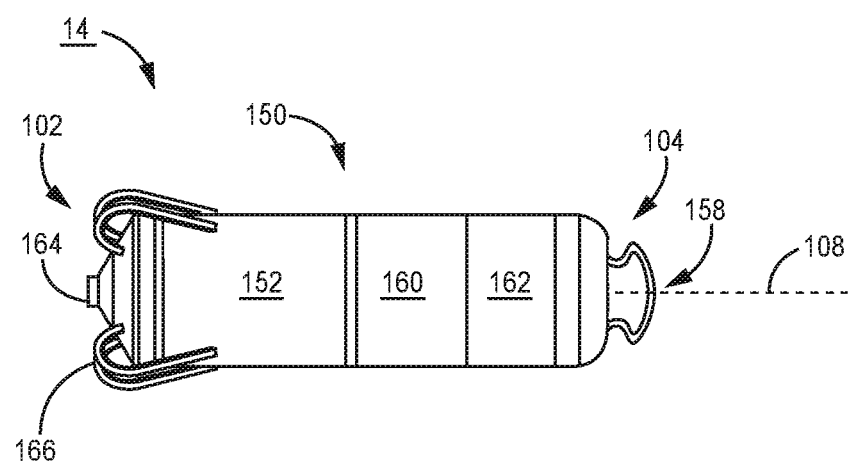
FIG. 2 is a conceptual diagram of the intracardiac pacemaker shown in FIG. 1.

FIG. 2 is a conceptual diagram of the intracardiac pacemaker 14 shown in FIG. 1. Pacemaker 14 includes electrodes 162 and 164 spaced apart along the housing 150 of pacemaker 14 for sensing cardiac electrical signals and delivering pacing pulses. Electrode 164 is shown as a tip electrode extending from a distal end 102 of pacemaker 14, and electrode 162 is shown as a ring electrode along a mid-portion of housing 150, for example adjacent proximal end 104. Distal end 102 is referred to as "distal" in that it is expected to be the leading end as pacemaker 14 is advanced through a delivery tool, such as a catheter, and placed against a targeted pacing site.

Electrodes 162 and 164 form an anode and cathode pair for bipolar cardiac pacing and sensing. In alternative embodiments, pacemaker 14 may include two or more ring electrodes, two tip electrodes, and/or other types of electrodes exposed along pacemaker housing 150 for delivering electrical stimulation to heart 8 and sensing cardiac electrical signals. Electrodes 162 and 164 may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 14 other than the locations shown.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. Electrode 164 may serve as a cathode electrode and be coupled to internal circuitry enclosed by housing 150, e.g., a pacing pulse generator and cardiac electrical signal sensing circuitry, via an electrical feedthrough crossing housing 150. Electrode 162 may be formed as a conductive portion of housing 150 defining a ring electrode that is electrically isolated from the other portions of the housing 150 as generally shown in FIG. 2. In other examples, the entire periphery of the housing 150 may function as an electrode that is electrically isolated from tip electrode 164, instead of providing a localized ring electrode such as anode electrode 162. Electrode 162 formed along an electrically conductive portion of housing 150 serves as a return anode during pacing and sensing.

The housing 150 includes a control electronics subassembly 152, which houses the electronics for sensing cardiac signals, producing pacing pulses and controlling therapy delivery and other functions of pacemaker 14 as described below in conjunction with FIG. 3. A motion sensor may be implemented as an accelerometer enclosed within housing 150 in some examples. The accelerometer provides a signal to a processor included in control electronics subassembly 152 for signal processing and analysis for detecting atrial systolic events for use in tachyarrhythmia detection and for timing ventricular pacing pulses in some examples.

The accelerometer may be a three-dimensional accelerometer having one "longitudinal" axis that is parallel to or aligned with the longitudinal axis 108 of pacemaker 14 and two, orthogonal axes that extend in radial directions relative to the longitudinal axis 108. Practice of the techniques disclosed herein, however, are not limited to a particular orientation of the accelerometer within or along housing 150. In other examples, a one-dimensional accelerometer may be used to obtain an intracardiac motion signal from which atrial systolic events are detected. In still other examples, a two dimensional accelerometer or other multi-dimensional accelerometer may be used. Each axis of a single or multi-dimensional accelerometer may be defined by a piezoelectric element, micro-electrical mechanical system (MEMS) device or other sensor element capable of producing an electrical signal in response to changes in acceleration imparted on the sensor element, e.g., by converting the acceleration to a force or displacement that is converted to the electrical signal. In a multi-dimensional accelerometer, the sensor elements may be arranged orthogonally with each sensor element axis orthogonal relative to the other sensor element axes. Orthogonal arrangement of the elements of a multi-axis accelerometer, however, is not necessarily required.

Each sensor element may produce an acceleration signal corresponding to a vector aligned with the axis of the sensor element. One, two or all three vector signals produced by a three dimensional accelerometer may be selected for use in detecting atrial systolic events for use in detecting and discriminating tachyarrhythmia and controlling atrial-synchronized ventricular pacing delivered by pacemaker 14.

Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 14 may include a set of fixation tines 166 to secure pacemaker 14 to patient tissue, e.g., by actively engaging with the ventricular endocardium and/or interacting with the ventricular trabeculae. Fixation tines 166 are configured to anchor pacemaker 14 to position electrode 164 in operative proximity to a targeted tissue for delivering therapeutic electrical stimulation pulses. Numerous types of active and/or passive fixation members may be employed for anchoring or stabilizing pacemaker 14 in an implant position. Pacemaker 14 may include a set of fixation tines as disclosed in commonly-assigned U.S. Pat. No. 9,775,872 (Grubac, et al.), hereby incorporated herein by reference in its entirety.

Pacemaker 14 may optionally include a delivery tool interface 158. Delivery tool interface 158 may be located at the proximal end 104 of pacemaker 14 and is configured to connect to a delivery device, such as a catheter, used to position pacemaker 14 at an implant location during an implantation procedure, for example within a heart chamber.

Figure 3:
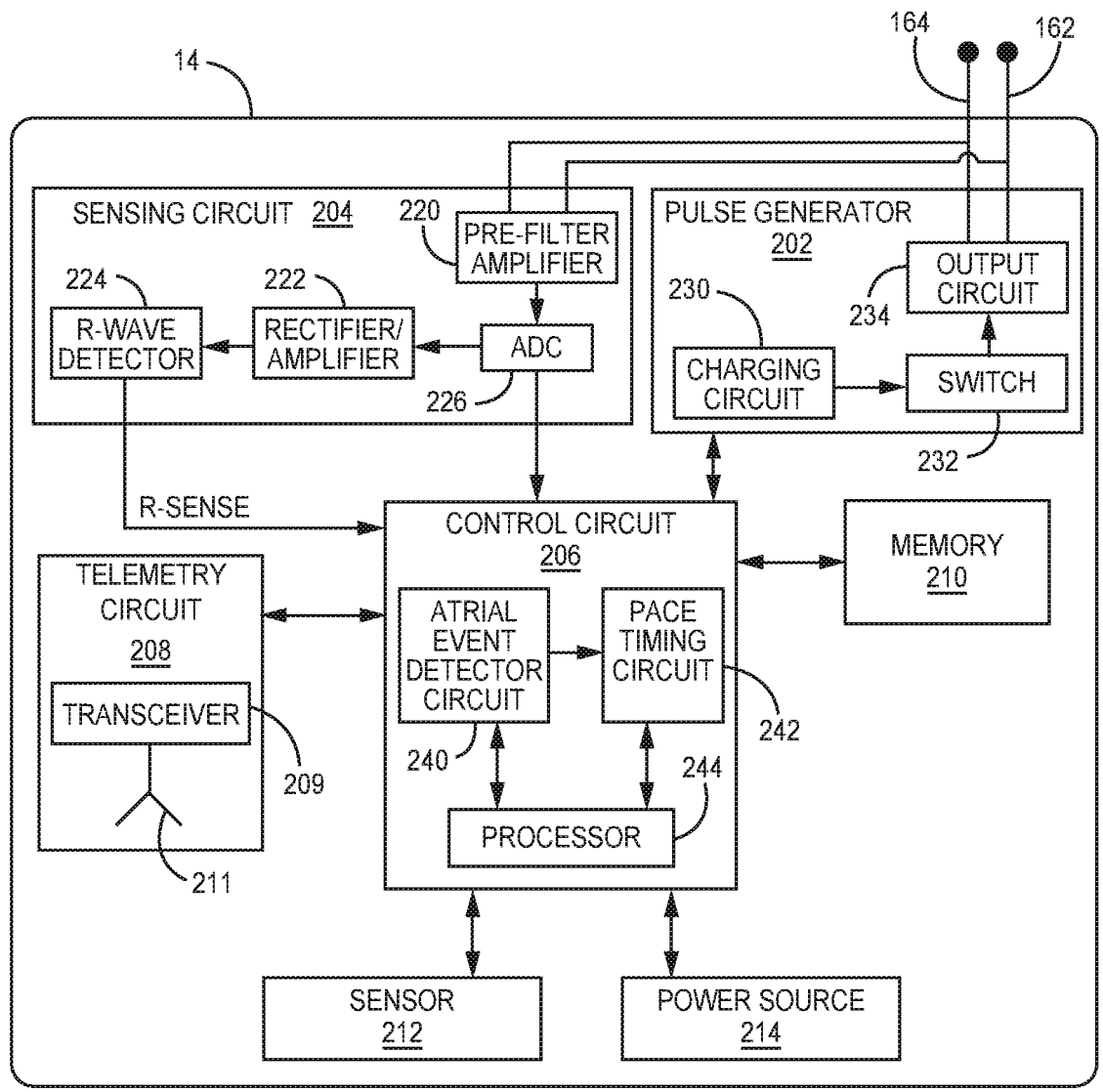
FIG. 3 is a schematic diagram of an example configuration of the pacemaker shown in FIG. 1.

FIG. 3 is a schematic diagram of an example configuration of pacemaker 14 shown in FIG. 1. Pacemaker 14 includes a pulse generator 202, a cardiac electrical signal sensing circuit 204, a control circuit 206, memory 210, telemetry circuit 208, sensor 212 and a power source 214. Sensor 212 is configured to produce an intraventricular signal including atrial mechanical event signals attendant to atrial mechanical systole. The illustrative examples described in conjunction with the accompanying drawings primarily refer to an intraventricular signal produced by a motion sensor. Sensor 212, therefore, may also be referred to herein as "motion sensor 212." The techniques disclosed herein, however, may be implemented in conjunction with other sensors capable of generating an intraventricular signal including atrial mechanical event signals. Examples of sensors that may be included in sensor 212 for sensing the mechanical atrial systolic events for use in determining an atrial arrhythmia score include motion sensors, such as piezoelectric sensors or MEMS devices, an impedance sensor capable of injecting an impedance drive current (or voltage) signal and sensing the resultant intraventricular voltage (or current) signal, or a pressure sensor for sensing an intraventricular pressure signal, as examples.

When sensor 212 is includes an impedance sensor, an atrial systolic event signal attendant to the mechanical atrial contraction or "atrial kick" may be detected from an intraventricular impedance signal using techniques for detecting the A-wave portion of an impedance signal as generally disclosed in U.S. Pat. No. 8,639,328 (Hettrick, et al.), incorporated herein by reference in its entirety. When sensor 212 includes a pressure sensor, an atrial systolic event signal attendant to the mechanical atrial contraction may be detected from the intraventricular pressure signal using techniques generally disclosed in U.S. Publication. No. 2011/0160787 (Greenhut, et al.). The atrial systolic events sensed from the intraventricular sensor signal may be used for determining an atrial event evidence score for use in atrial tachyarrhythmia detection as described below.

In some examples, sensor 212 may include a multi-axis accelerometer, e.g., a two-dimensional or three-dimensional accelerometer, with each axis providing a signal that may be analyzed individually or in combination for detecting cardiac mechanical events. Motion sensor 212 produces an electrical signal correlated to motion or vibration of sensor 212 (and pacemaker 14), e.g., when subjected to flowing blood, cardiac motion and patient physical activity. The motion sensor 212 may include one or more filter, amplifier, rectifier, analog-to-digital converter (ADC) and/or other components for producing a motion signal that is passed to control circuit 206. For example, each vector signal corresponding to each individual axis of a multi-axis accelerometer may be filtered by a high pass filter, e.g., a 10 Hz high pass filter, digitized by an ADC and rectified for use by atrial event detector circuit 240 for detecting atrial systolic events. The high pass filter may have a higher or lower cutoff frequency, e.g., 5 Hz, if needed to detect atrial signals that have higher or lower frequency content in other examples. In some examples, high pass filtering is performed with no low pass filtering. In other examples, each accelerometer axis signal is filtered by a low pass filter, e.g., a 30 Hz low pass filter, with or without high pass filtering.

One example of an accelerometer for use in implantable medical devices that may be included in motion sensor 212 is generally disclosed in U.S. Pat. No. 5,885,471 (Ruben, et al.), incorporated herein by reference in its entirety. An implantable medical device arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers that may be implemented in pacemaker 14 and used for detecting cardiac mechanical events using the presently disclosed techniques are generally described in U.S. Pat. No. 5,593,431 (Sheldon) and U.S. Pat. No. 6,044,297 (Sheldon), both of which are incorporated herein by reference in their entirety. Other accelerometer designs may be used for producing an electrical signal that is correlated to motion imparted on pacemaker 14 due to ventricular and atrial events.

The various circuits represented in FIG. 3 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Sensing circuit 204 is configured to receive a cardiac electrical signal via electrodes 162 and 164 by a pre-filter and amplifier circuit 220. Pre-filter and amplifier circuit may include a high pass filter to remove DC offset, e.g., a 2.5 to 5 Hz high pass filter, or a wideband filter having a passband of 2.5 Hz to 100 Hz to remove DC offset and high frequency noise. Pre-filter and amplifier circuit 220 may further include an amplifier to amplify the "raw" cardiac electrical signal passed to analog-to-digital converter (ADC) 226. ADC 226 may pass a multi-bit, digital electrogram (EGM) signal to control circuit 206 for use by atrial event detector circuit 240 and/or processor 244 in identifying ventricular electrical events (e.g., R-waves or T-waves) and/or atrial electrical events, e.g., P-waves. Identification of cardiac electrical events may be used for detecting atrial systolic events from the motion sensor signal and in determining cardiac event intervals for use in detecting and discriminating ventricular tachyarrhythmia from SVT. The digital signal from ADC 226 may be passed to rectifier and amplifier circuit 222, which may include a rectifier, bandpass filter, and amplifier for passing a cardiac signal to R-wave detector 224.

R-wave detector 224 may include a sense amplifier or other detection circuitry that compares the incoming rectified, cardiac electrical signal to an R-wave sensing threshold, which may be an auto-adjusting threshold. When the incoming signal crosses the R-wave sensing threshold, the R-wave detector 224 produces an R-wave sensed event signal (R-sense) that is passed to control circuit 206. In other examples, R-wave detector 224 may receive the digital output of ADC 226 for detecting R-waves by a comparator, morphological signal analysis of the digital EGM signal or other R-wave detection techniques. Processor 244 may provide sensing control signals to sensing circuit 204, e.g., R-wave sensing threshold, sensitivity, and various blanking and refractory intervals applied to the cardiac electrical signal for controlling R-wave sensing. R-wave sensed event signals passed from R-wave detector 224 to control circuit 206 may be used for scheduling ventricular pacing pulses by pace timing circuit 242 and for determining VCLs for use in atrial tachyarrhythmia detection as described below. The R-wave sensed event signals received from R-wave detector 224 may also be used by atrial event detector circuit 240 in detecting atrial systolic events from a signal received from motion sensor 212. For example, R-wave sensed event signals may be used in setting one or more timing windows to facilitate atrial event sensing from the motion signal and to determine of how many atrial events are sensed during a single VCL.

Control circuit 206 includes an atrial event detector circuit 240, pace timing circuit 242, and processor 244. Atrial event detector circuit 240 is configured to detect atrial mechanical events, and in particular atrial systolic events, from a signal received from motion sensor 212. In some examples, one or more ventricular mechanical events may be detected from the motion sensor signal in a given cardiac cycle to facilitate positive detection of the atrial systolic event from the motion sensor signal during the ventricular cycle.

Control circuit 206 may receive R-wave sensed event signals and/or digital cardiac electrical signals from sensing circuit 204 for use in detecting and confirming cardiac events and controlling ventricular pacing. R-wave sensed event signals may be passed to pace timing circuit 242 for inhibiting scheduled ventricular pacing pulses or scheduling ventricular pacing pulses when pacemaker 14 is operating in a non-atrial tracking ventricular pacing mode. Pace timing circuit 242 may determine time intervals between consecutively received R-wave sensed event signals, referred to herein as RR intervals or RRIs, for use by processor 244 in a tachyarrhythmia detection. As described below, differences between consecutive ventricular cycle lengths (VCLs) may be determined for use in determining a metric of VCL irregularity as evidence of AF. A VCL may be an RRI, the time interval between a ventricular pacing pulse and an R-wave sensed event signal, or the time interval between two consecutive ventricular pacing pulses.

R-wave sensed event signals may be passed to atrial event detector circuit 240 for use in setting time windows used by control circuit 206 in detecting atrial systolic events from the motion sensor signal. Atrial event detector circuit 240 receives a motion signal from motion sensor 212 and may start an atrial blanking period in response to a ventricular electrical event, e.g., an R-wave sensed event signal from sensing circuit 204 or delivery of a pacing pulse by pulse generator 202. The blanking period may correspond to a time period after the ventricular electrical event during which ventricular mechanical events, e.g., corresponding to ventricular contraction and isovolumic relaxation are expected to occur. Motion signal peaks that occur during the atrial blanking period are not sensed as atrial events to avoid falsely sensing a ventricular motion signal event as the atrial systolic event.

Atrial event detector circuit 240 determines if the motion sensor signal satisfies atrial mechanical event detection criteria outside of the atrial blanking period. The motion sensor signal during the blanking period may be monitored by atrial event detector circuit 240 and/or processor 244 for the purposes of detecting ventricular mechanical events, which may be used for confirming or validating atrial systolic event detection or detecting ventricular event intervals in some examples. As such, ventricular mechanical event detection windows may be set during the atrial blanking period and may be set according to predetermined time intervals following identification of a ventricular electrical event. Control circuit 206 may be configured to detect one or more ventricular mechanical events during respective ventricular event detection windows during the atrial blanking period. The timing and detection of the ventricular mechanical events may be used to update the atrial blanking period and/or may be used to confirm detection of the atrial event occurring subsequent to expected ventricular mechanical events.

Atrial event detector circuit 240 may set time windows corresponding to the passive ventricular filling phase and the active ventricular filling phase based on the timing of a preceding ventricular electrical event, either an R-wave sensed event signal or a ventricular pacing pulse. A motion sensor signal crossing of an atrial event sensing threshold during either of these windows may be detected as the atrial systolic event. As described below, two different atrial event sensing threshold values may be established for applying during the passive filling phase window and after the passive filling phase window (during an active filling phase window).

Atrial event detector circuit 240 passes an atrial event detection signal to processor 244 and/or pace timing circuit 242 in response to detecting an atrial event. Processor 244 may include one or more clocks for generating clock signals that are used by pace timing circuit 242 to time out an AV pacing interval that is started upon receipt of an atrial event detection signal from atrial event detector circuit 240. Pace timing circuit 242 may include one or more pacing escape interval timers or counters that are used to time out the AV pacing interval, which may be a programmable interval stored in memory 210 and retrieved by processor 244 for use in setting the AV pacing interval used by pace timing circuit 242.

Pace timing circuit 242 may additionally include a lower pacing rate interval timer for controlling a minimum ventricular pacing rate. For example, if an atrial systolic event is not detected from the motion sensor signal triggering a ventricular pacing pulse at the programmed AV pacing interval, a ventricular pacing pulse may be delivered by pulse generator 202 upon expiration of the lower pacing rate interval to prevent ventricular asystole and maintain a minimum ventricular rate. At times, control circuit 206 may control pulse generator 202 in a non-atrial tracking ventricular pacing mode (also referred to as "asynchronous ventricular pacing"). The non-atrial tracking ventricular pacing mode may be denoted as a VDI pacing mode in which ventricular pacing pulses are delivered in the absence of a sensed R-wave and inhibited in response to an R-wave sensed event signal from sensing circuit 204. Dual chamber sensing may be performed during the non-atrial tracking ventricular pacing mode by sensing ventricular electrical events by sensing circuit 204 and sensing atrial events by atrial event detector circuit 240 receiving a motion signal from motion sensor 212.

Processor 244 may receive atrial sensed event signals from atrial event detector circuit 240 and R-wave sensed event signals from sensing circuit 204 for use in tachyarrhythmia detection. Processor 244 may determine differences between consecutive VCLs for determining VCL irregularity. In some examples, two consecutively determined VCL differences define an ordered pair of (x, y) coordinates of a point plotted in a two dimensional Lorenz plot. The clustering and distribution of Lorenz plot points determined from a series of VCL differences may be analyzed to determine a metric or score of VCL variability as evidence for an atrial tachyarrhythmia, e.g., AF. The metric or score may be described herein as an atrial arrhythmia score. In general, an atrial arrhythmia score provides an indication of atrial arrhythmia and is correlated to the presence of atrial arrhythmia and may be based on VCL irregularity.

In some examples, an AF evidence score (also referred to herein as an atrial arrhythmia score) may be determined from VCL differences as generally disclosed in U.S. Pat. No. 7,627,368 (Houben, et al), U.S. Pat. No. 7,031,765 (Ritscher, et al.), U.S. Pat. No. 7,537,569 (Sarkar, et al.) and U.S. Pat. No. 7,623,911 (Sarkar, et al.) as examples, all of which are incorporated herein by reference in their entirety. In response to receiving detected atrial mechanical event signals from atrial event detector circuit 240, processor 244 may determine a second atrial arrhythmia score, also referred to herein as an atrial event score, which may be evidence against an atrial arrhythmia because distinct atrial mechanical event signals attendant to atrial systole are expected to occur at a very low frequency or be non-existent during AF. The second atrial arrhythmia score, or atrial event score, may be used to adjust the AF evidence score to decrease the likelihood of detecting AF during a period of irregular VCLs. In some examples, absence of an atrial mechanical event signal is evidence supporting an AF detection and may be used to increase the likelihood of detecting AF, for example by reducing the criteria or requirements for detecting AF based on the AF evidence score. Accordingly, the second atrial arrhythmia score may be inversely correlated to a presence of atrial arrhythmia in some examples.

Pulse generator 202 generates electrical pacing pulses that are delivered to the RV of the patient's heart via cathode electrode 164 and return anode electrode 162. In addition to providing control signals to pace timing circuit 242 and pulse generator 202 for controlling the timing of ventricular pacing pulses, processor 244 may retrieve programmable pacing control parameters, such as pacing pulse amplitude and pacing pulse width, which are passed to pulse generator 202 for controlling pacing pulse delivery. Pulse generator 202 may include charging circuit 230, switching circuit 232 and an output circuit 234.

Charging circuit 230 may include a holding capacitor that may be charged to a pacing pulse amplitude by a multiple of the battery voltage signal of power source 214 under the control of a voltage regulator. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of an AV pacing interval (or VV lower rate pacing interval) and kept closed for a programmed pacing pulse width to enable discharging of the holding capacitor of charging circuit 230. The holding capacitor, previously charged to the pacing pulse voltage amplitude, is discharged across electrodes 162 and 164 through the output capacitor of output circuit 234 for the programmed pacing pulse duration. Examples of pacing circuitry generally disclosed in U.S. Pat. No. 5,507,782 (Kieval, et al.) and in U.S. Pat. No. 8,532,785 (Crutchfield, et al.), both of which patents are incorporated herein by reference in their entirety, may be implemented in pacemaker 14 for charging a pacing capacitor to a predetermined pacing pulse amplitude under the control of control circuit 206 and delivering a pacing pulse.

Control circuit 206 may be configured to control pulse generator 202 to deliver ventricular pacing pulses according to an atrial-tracking ventricular pacing mode, sometimes referred to as a VDD mode, or according to a non-atrial tracking ventricular pacing mode, e.g., VDI(R) or VVI(R). Control circuit 206 may control pacing mode switching between an atrial-tracking and a non-atrial tracking pacing mode. For example, pacemaker 14 may switch from an atrial-tracking ventricular pacing mode to a non-atrial tracking ventricular pacing mode in response to detecting high patient activity or loss of atrial event sensing. Methods for controlling pacing mode switching in an intracardiac ventricular pacemaker having a motion sensor are generally disclosed in U.S. Pat. No. 9,399,140 (Cho, et al) and in U.S. patent application Ser. No. 15/366,933 (Demmer, et al.), both of which are incorporated herein by reference in their entirety.

In some examples, pacemaker 14 may be configured to deliver anti-tachycardia pacing (ATP) in response to detecting VT. VT may be detected in response to a predetermined number of RRIs being within a VT interval zone and AF detection criteria not being met. As described herein, during a fast or irregular ventricular rate, AF detection criteria may be unmet when at least one atrial event is detected from the motion sensor signal. If VT criteria are met and AF detection criteria are unmet due to atrial event sensing from the motion signal, control circuit 206 may control pulse generator 202 to deliver one or more sequences of ATP therapy.

Memory 210 may include computer-readable instructions that, when executed by control circuit 206, cause control circuit 206 to perform various functions attributed throughout this disclosure to pacemaker 14. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media. Memory 210 may store timing intervals and other data used by control circuit 206 to control the delivery of pacing pulses by pulse generator 202, e.g., by detecting an atrial event by atrial event detector circuit 240 from the motion sensor signal and setting a pacing escape interval timer included in pace timing circuit 242.

Memory 210 may be configured to store tachyarrhythmia episode data for transmission to external device 20. In some examples, in response to detecting AF, control circuit 206 may store a segment of the ventricular EGM signal and/or motion sensor signal and/or store data relating to atrial tachyarrhythmia episode detections such as updating an atrial tachyarrhythmia or AF burden metric, storing the number and duration of detected atrial tachyarrhythmia episodes, or the like. Control circuit 206 may store similar data associated with ventricular tachyarrhythmia episode detections, such as VT episode recordings of the EGM signal and/or motion signal, the number of VT episodes detected and respective VT episode duration as well as any delivered ATP therapy and therapy outcome.

In some examples, control circuit 206 may be configured to generate an alert or notification in response to detecting an atrial tachyarrhythmia or when the atrial tachyarrhythmia burden reaches a threshold level, e.g. x minutes out of the most recent 24 hours. The alert may be transmitted to external device 20 via telemetry circuit 208 to notify the patient and/or a clinician of the detected atrial tachyarrhythmia. A VT alert may be generated in response to detecting one or more VT episodes.

Power source 214, which may be included in battery subassembly 160, provides power to each of the other circuits and components of pacemaker 14 as required. Power source 214 may include one or more energy storage devices, such as one or more rechargeable or non-rechargeable batteries. The connections between power source 214 and other pacemaker circuits and components are not shown in FIG. 3 for the sake of clarity but are to be understood from the general block diagram of FIG. 3. For example, power source 214 may provide power as needed to charging and switching circuitry included in pulse generator 202; amplifiers, ADC 226 and other components of sensing circuit 204; telemetry circuit 208; memory 210, and motion sensor 212.

Telemetry circuit 208 includes a transceiver 209 and antenna 211 for transferring and receiving data, e.g., via a radio frequency (RF) communication link. Telemetry circuit 208 may be capable of bi-directional communication with external device 20 (FIG. 1) as described above. Programmable control parameters for controlling and performing various pacemaker functions, such as atrial event detection, ventricular pacing, tachyarrhythmia detection and associated response(s) such as generating notifications or alerts or controlling therapy, may be received by telemetry circuit 208 and stored in memory 210 for access by control circuit 206. Intraventricular signals sensed by sensor 212, e.g., motion sensor signals, and cardiac electrical signals and/or data derived therefrom may be transmitted by telemetry circuit 208 to external device 20. For example, control circuit 206 may generate an atrial arrhythmia episode notification and/or update atrial arrhythmia episode data stored in memory 201 and control telemetry circuit 206 to transmit the notification and/or updated atrial arrhythmia episode data to external device 20 for generating a display of the atrial arrhythmia episode data. The atrial arrhythmia episode data may include recordings of intraventricular signals including an indication of sensed atrial systolic events, cardiac electrical signals including an indication of sensed R-waves, atrial arrhythmia episode duration, atrial arrhythmia burden, a number of atrial arrhythmia episodes detected and/or other atrial arrhythmia episode data. A display of the data provides useful diagnostic information for a clinician in selecting or managing therapy for the patient.

The functions attributed to pacemaker 14 herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. For example, atrial systolic event detection from the motion sensor signal, ventricular pacing control operations, and tachyarrhythmia detection performed by pacemaker 14 may be implemented in control circuit 206 executing instructions stored in memory 210 and relying on input from sensing circuit 204 and motion sensor 212. Providing software, hardware, and/or firmware to accomplish the described functionality in the context of any modern pacemaker, given the disclosure herein, is within the abilities of one of skill in the art.

Figure 4:
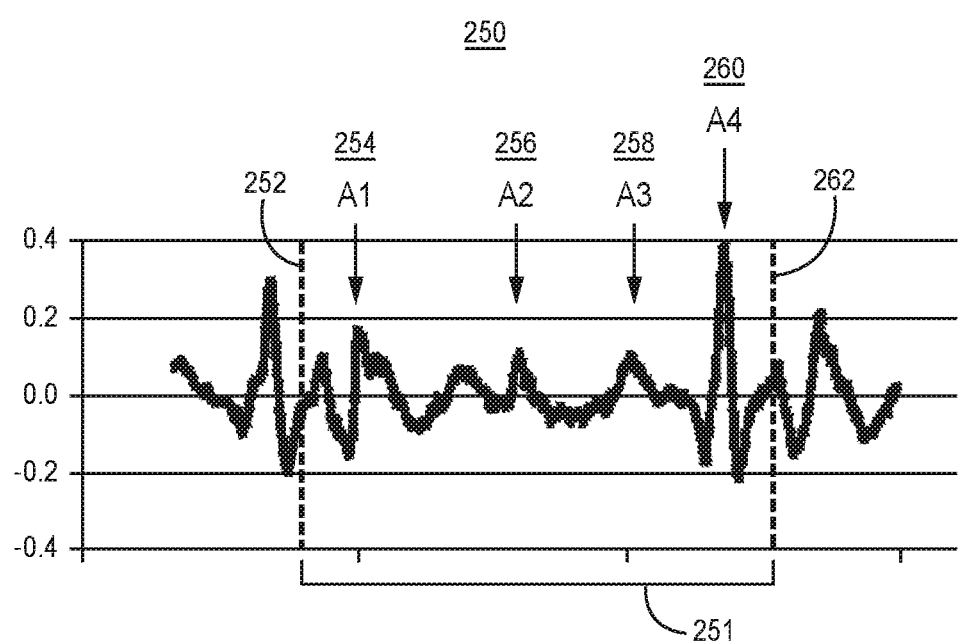
FIG. 4 is an example of a motion signal that may be produced by a motion sensor included in the pacemaker of FIG. 1 over a cardiac cycle.

FIG. 4 is an example of a motion sensor signal 250 that may be produced by motion sensor 212 over a cardiac cycle during normal sinus rhythm or atrial synchronized ventricular pacing. Vertical dashed lines 252 and 262 denote the timing of two consecutive ventricular events (an intrinsic ventricular depolarization or a ventricular pace), marking the respective beginning and end of the ventricular cycle 251. The motion signal includes an A1 event 254, an A2 event 256, an A3 event 258 and an A4 event 260. The A1 event 254 is an acceleration signal (in this example when motion sensor 212 is implemented as an accelerometer) that occurs during ventricular contraction and marks ventricular mechanical systole. The A1 event is also referred to herein as a "ventricular contraction event." The A2 event 256 is an acceleration signal that may occur during closure of the aortic and pulmonic valves and marks the approximate offset or end of ventricular mechanical systole. The A2 event may also mark the beginning of ventricular diastole and is generally an indication of the isovolumic relaxation phase of the ventricles that occurs with aortic and pulmonic valve closure. The A1 and A2 events may mark the start and end, respectively, of a systolic time interval.

The A3 event 258 is an acceleration signal that occurs during passive ventricular filling and marks ventricular mechanical diastole. The A3 event is also referred to herein as the "A3 signal" and as the "ventricular passive filling event." Since the A2 event occurs with the end of ventricular systole, it is an indicator of the onset of ventricular diastole. The A3 event occurs during ventricular diastole. As such, the A2 and A3 events may be collectively referred to as ventricular mechanical diastolic events because they are both indicators of the ventricular diastolic period.

The A4 event 260 is an acceleration signal that occurs during atrial contraction and active ventricular filling and marks atrial mechanical systole. The A4 event 260, also referred to herein as the "A4 signal," is the "atrial systolic event" or merely the "atrial event" that is detected from motion sensor signal 250. Atrial event detector circuit 240 detects A4 event 260 and may pass an atrial sensed event signal to processor 244 for use in atrial tachyarrhythmia detection. In some examples, the A4 event signal is used by pace timing circuit 242 to trigger a ventricular pacing pulse by starting an AV pacing interval in response to detecting the A4 event 260. Control circuit 206 may be configured to detect one or more of the A1, A2, and A3 events from motion sensor signal 250, for at least some ventricular cardiac cycles, for use in positively detecting the A4 event 260 and setting atrial event detection control parameters. The A1, A2 and/or A3 events may be detected and characterized to avoid false detection of A4 events and promote reliable A4 event detection, e.g., for promoting a high confidence of A4 event detection during atrial tachyarrhythmia detection and for proper timing of atrial-synchronized ventricular pacing pulses. In some examples, the A1 or A2 events may be used for determining VCLs, instead of or in addition to R-waves sensed from the cardiac electrical signal.

Figure 5:
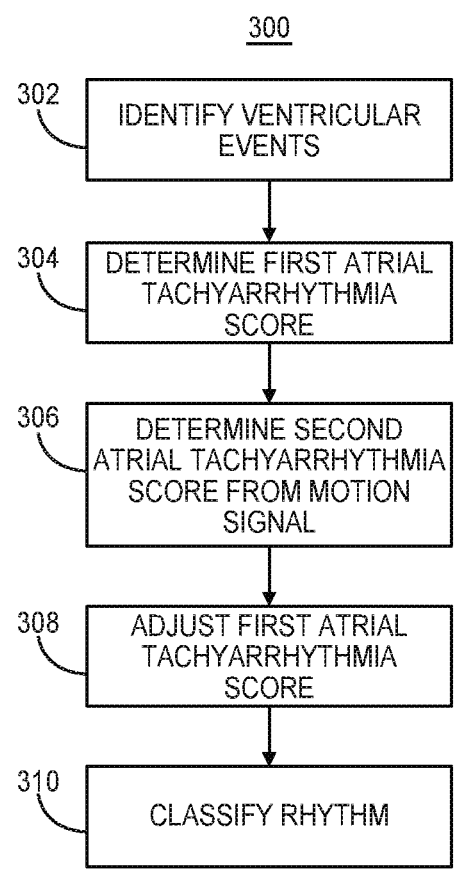
FIG. 5 is a flow chart of a method for detecting a cardiac arrhythmia that may be performed by the pacemaker of FIG. 1 according to one example.

FIG. 5 is a flow chart 300 of a method for detecting a cardiac arrhythmia that may be performed by pacemaker 14 according to one example. At block 302, control circuit 206 identifies ventricular events. The ventricular events may include sensed R-waves, ventricular pacing pulses, or A1 or A2 events sensed from the motion signal. Control circuit 206 determines a first atrial tachyarrhythmia score at block 304 based on the identified ventricular events. The first atrial tachyarrhythmia score may be based on VCLs determined between consecutive pairs of identified ventricular events in some examples. As described below, the first atrial tachyarrhythmia score may be based on patterns of consecutive VCL differences. The first atrial tachyarrhythmia score determined at block 304 based on VCLs may be positively correlated with the occurrence of atrial tachyarrhythmia, e.g., irregular VCLs occurring during AF. In this case a relatively higher first atrial tachyarrhythmia score corresponds to an increased probability of the atrial tachyarrhythmia being present.

At block 306, control circuit 206 determines a second atrial tachyarrhythmia score from the motion signal received from motion sensor 212. In some examples, the second atrial tachyarrhythmia score may be negatively correlated with the occurrence of an atrial tachyarrhythmia. For example the second atrial tachyarrhythmia score may be increased in response to detecting A4 signals from the motion signal as evidence of atrial systolic beats, which is evidence against the rhythm being AF. For example, if the A4 signal amplitude is a consistent 0.2 g units (1 g being the acceleration of gravity) and then drops by more than 50% to less than 0.1 g units during AF, the A4 events will no longer be detected. If one or more A4 events are being detected, the rhythm is unlikely to be AF.

In other examples, the second atrial tachyarrhythmia score based on the motion signal may also be positively correlated with the occurrence of an atrial arrhythmia, in which case it may increase when an atrial tachyarrhythmia is likely to be present. For example, the second atrial arrhythmia score may be increased in response to detecting shortening of a systolic time interval from the motion signal.

As described below, the systolic time interval may be determined from the motion signal as an A1-A2 interval extending between an A1 event 254 and an A2 event 256 (as seen in FIG. 4). Detection of a shortened systolic time interval may be positive evidence for the detection of an atrial tachyarrhythmia, e.g., AF. In this case, the second atrial tachyarrhythmia score may be increased when A1-A2 interval shortening is detected and be positively correlated with atrial tachyarrhythmia.

In another example, if multiple A4 events are sensed during a single VCL, the presence of the multiple A4 events may indicate atrial flutter. The second atrial tachyarrhythmia score may be increased in response to detecting multiple A4 events within a single VCL and be positive evidence for the detection of an atrial tachyarrhythmia, e.g., atrial flutter.

At block 308, control circuit 206 may adjust the first atrial arrhythmia score based on the second atrial arrhythmia score. For example, the first atrial arrhythmia score may be decreased by the second atrial arrhythmia score when the first score is positively correlated with atrial tachyarrhythmia and the second score is negatively correlated with atrial tachyarrhythmia. As described below, the first atrial tachyarrhythmia score may be an AF evidence score determined from VCLs and is increased during periods of VCL irregularity, which can occur during AF. The second atrial tachyarrhythmia score may be an atrial event evidence score determined by counting A4 events sensed from the motion signal during the VCLs. As the atrial event evidence score increases, indicating the occurrence of atrial systolic events that would not be detected during AF, the probability of the rhythm being AF decreases. Thus, the second atrial arrhythmia score may be subtracted from the first atrial arrhythmia score at block 306.

In examples where the second atrial arrhythmia score is positively correlated to the presence of atrial tachyarrhythmia, the second atrial tachyarrhythmia score may be added to the first atrial tachyarrhythmia score at block 308. For instance if the second atrial tachyarrhythmia score is increased in response to detecting shortening of the systolic time interval between the A1 and A2 events, or in response to detecting multiple A4 events within a single VCL, the first atrial tachyarrhythmia score may be increased by adding the second atrial tachyarrhythmia score at block 308.

At block 310, the heart rhythm may be classified as either an atrial tachyarrhythmia or a non-atrial tachyarrhythmia based on the adjusted first atrial arrhythmia score. Various examples are described below for classifying the heart rhythm based on the adjusted first atrial tachyarrhythmia score and subsequently detecting an atrial tachyarrhythmia and responding to the atrial tachyarrhythmia detection. For example, the first atrial tachyarrhythmia score, adjusted by the second atrial tachyarrhythmia score, may be determined for one or more time segments of the cardiac electrical signal and/or the motion signal. The adjusted first atrial tachyarrhythmia score may be compared to a threshold value for classifying the heart rhythm during the time segment. As further described below, the control circuit 206 may adjust the threshold value that is compared to the first atrial tachyarrhythmia score based on an analysis of the motion signal to increase or decrease the likelihood of detecting an atrial tachyarrhythmia based on the first atrial tachyarrhythmia score. One or more time segments may be required to be classified as atrial tachyarrhythmia in order to make an atrial tachyarrhythmia detection and provide a response to the atrial tachyarrhythmia detection.

Figure 6:
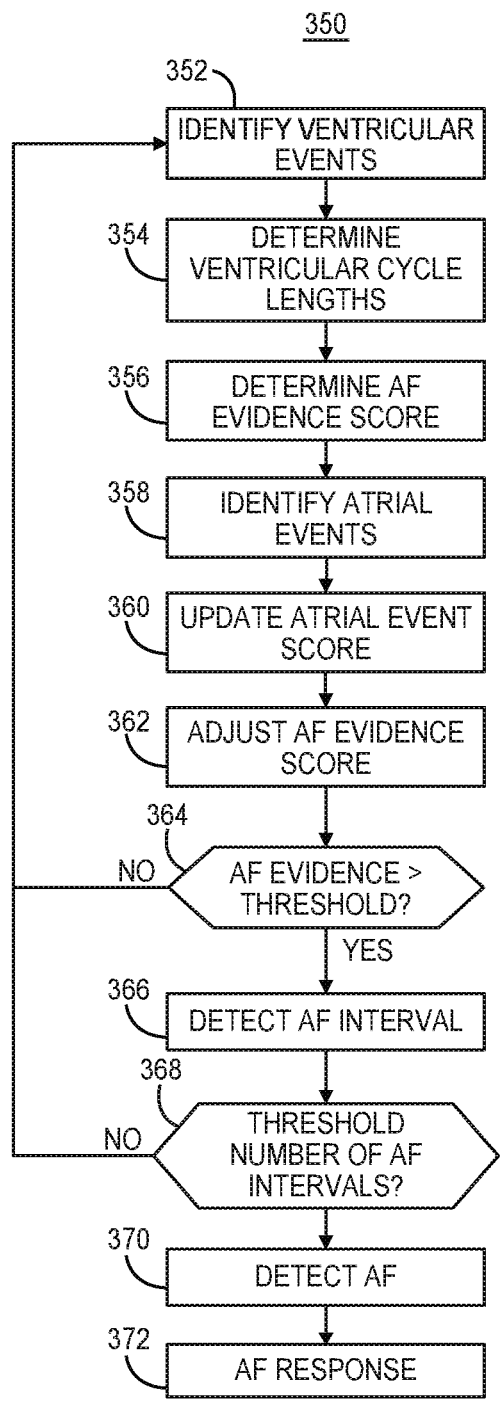
FIG. 6 is a flow chart of a method for detecting a tachyarrhythmia according to another example.

FIG. 6 is a flow chart 350 of a method for detecting tachyarrhythmia according to one example. Control circuit 206 may perform the method of flow chart 350 for monitoring for atrial tachyarrhythmia on an ongoing basis. In other examples, control circuit 206 may perform the method of FIG. 6 periodically for re-determining the presence of a previously detected atrial tachyarrhythmia. The atrial tachyarrhythmia detection methods disclosed in conjunction with FIG. 6 and other flow charts and diagrams presented herein may be performed when pacemaker 14 is operating in a non-atrial tracking (asynchronous) ventricular pacing mode, e.g., a VDI pacing mode. In some examples, the atrial tachyarrhythmia detection may be performed in both atrial-tracking (synchronous) and non-atrial tracking ventricular pacing modes. When operating in either an atrial synchronous or atrial asynchronous pacing mode, a pacing interlock may be implemented which prevents an atrial tachyarrhythmia detection to be made when a threshold percentage of ventricular events are paced ventricular cycles. In this way, during a VDD pacing mode, for example, when A4 events are being sensed regularly resulting in frequent synchronized ventricular pacing greater than the pacing interlock threshold percentage, the atrial tachyarrhythmia is precluded from being detected.

At block 352, control circuit 206 identifies a ventricular event for determining a ventricular cycle length (VCL) at block 354. The ventricular event may be a ventricular pacing pulse or a sensed R-wave. For example, control circuit 206 may receive an R-wave sensed event signal from sensing circuit 204. At block 354, the VCL between the received R-wave sensed event signal and the most recent preceding ventricular electrical event, e.g., the most recently preceding ventricular pacing pulse or R-wave sensed event signal, is determined as the VCL.

The VCL may be determined between two intrinsic, sensed R-waves, between an intrinsic sensed R-wave and a ventricular pacing pulse and in some cases between two ventricular pacing pulses. The method of FIG. 6 and the atrial tachyarrhythmia detection techniques described in conjunction with other flow charts and diagrams presented herein generally refer to determination of VCL based on ventricular electrical events, e.g., sensed, intrinsic R-waves and ventricular pacing pulses. However, it is to be understood that VCLs may be determined from mechanical events detected from the motion signal received from motion sensor 212 in other examples. For example, a VCL may be determined as an A1-A1 interval or an A2-A2 interval (see A1 event 254 and A2 event 256 in FIG. 4).

At block 356, control circuit 206 may determine an AF evidence score based on VCLs acquired over a predetermined time interval or based on a most recent predetermined number of VCLs. One method for determining an AF evidence score is described briefly in conjunction with FIG. 8 below and other example techniques for determining an AF score are disclosed in the above-incorporated U.S. Pat. No. 7,627,368 (Houben, et al), U.S. Pat. No. 7,031,765 (Ritscher, et al.), U.S. Pat. No. 7,537,569 (Sarkar, et al.) and U.S. Pat. No. 7,623,911 (Sarkar, et al.). The AF evidence score may be determined based on a distribution of the differences between consecutive VCLs. Generally, a more disperse distribution of VCL differences is evidence of VCL irregularity and supports a detection of AF.

At block 358, control circuit 206 may determine if atrial events are detected from the motion signal during the VCLs used to determine the AF evidence score. In particular, control circuit 206 may determine how many VCLs include exactly one A4 event sensed during a single, respective VCL. Control circuit 206 updates an atrial event evidence score at block 360 based on atrial events sensed from the motion signal. The atrial event evidence score may be a metric that indicates the number of atrial events that are detected with a high degree of certainty during the predetermined time interval or predetermined number of VCLs. The presence of clear or well-defined atrial systolic event signals in the motion signal, particularly one single sensed A4 event per VCL, is evidence against an AF rhythm since atrial fibrillation will not produce the active atrial filling or atrial kick that results in the A4 event signal in the intraventricular motion sensing signal.

As the atrial event evidence score increases, the less likely that a true AF rhythm is present. Any irregularity in VCLs that may be causing the AF evidence score to be high may be more likely due to a ventricular tachyarrhythmia, runs of atrial or ventricular ectopy, or other abnormal heart rhythm other than AF. As such, the atrial event evidence score is used to adjust the AF evidence score at block 362. In some examples, the atrial event evidence score is subtracted from the AF evidence score such that the higher the atrial event evidence score, due to a correspondingly higher number of sensed atrial events during the VCLs, the more the AF evidence score may be decreased. In other examples, a single sensed atrial event or a predetermined number of sensed atrial events sensed during the VCLs used to determine the AF evidence score may cause control circuit 206 to adjust the AF evidence score by a predetermined decrement. In some examples, the AF evidence score is decreased by the atrial event evidence score only when the AF evidence score is greater than a predetermined threshold and/or the atrial event evidence score is greater than a predetermined threshold. Other methods may be used for adjusting the AF evidence score based on the atrial event evidence score for generally decreasing the likelihood of detecting AF when at least one atrial systolic event is detected from the motion signal during the VCLs used to determine the AF evidence score.

The AF evidence score is compared to an AF detection threshold at block 364. If the AF evidence score, after adjusting by the atrial event evidence score as needed, is less than the AF evidence detection threshold, the process returns to block 352 to continue determining VCLs for determining the next AF evidence score. If the AF evidence score is greater than the AF evidence detection threshold, control circuit 206 may classify the interval over which the VCLs were determined as an AF interval at block 366. If a threshold number of AF intervals are detected (block 368), AF is detected at block 370. The threshold number of AF intervals required to detect AF may be one or more. When two or more AF intervals are required to be classified as AF intervals in order to detect AF, the AF intervals may or may not be required to be consecutive. In some examples, the techniques for detecting AF based on time intervals that are classified as AF (or not) as generally disclosed in U.S. Publication No. 2018/0028086 (Cao, et al.) may be used in combination with the techniques of adjusting the AF evidence score based on analysis of the motion signal as disclosed herein. The '086 publication is incorporated herein by reference in its entirety.

In other examples, rather than adjusting the AF evidence score by the atrial event evidence score, control circuit 206 may use the AF evidence score and the atrial event evidence score in one or more logic operations for detecting AF. For instance, in one logic operation the AF evidence score is required to be equal to or greater than an AF detection threshold, and the atrial event evidence score is required to be less than an atrial event threshold in order to detect AF. If either of these criteria is not met, AF is not detected. Multiple logic operations may be performed using different tiered combinations of AF detection threshold and atrial event threshold. For instance, if the AF evidence score is less than a first AF detection threshold, the atrial event evidence score may be compared to a second lower atrial event threshold. If the atrial event evidence score is less than the second lower atrial event threshold and the AF evidence score is greater than a second, lower AF detection threshold, AF may still be detected.

Pacemaker 14 may be configured to provide an AF detection response at block 372. The AF detection response may include generating an AF detection notification and/or storing AF episode related data such as a time and date stamp of the AF detection, a time duration of the AF episode, the ventricular rate during the AF episode, or other AF episode related data. The AF detection response may include storing a time segment of the cardiac electrical signal and/or intraventricular motion signal acquired during the detected AF episode. The stored signal data and/or other AF episode data may be transmitted to an external device, e.g., external device 20, for generating a display of the atrial arrhythmia episode data for review by a clinician. In some examples, control circuit 206 may be configured to sum the time duration of all AF episodes detected over a predetermined time period, e.g., over 24 hours, one week, one month or other time period. The cumulative time durations of AF episodes may be stored in memory 210 as an AF burden that is updated in response to each AF detection and may be transmitted to the external device 20.

In addition to, or alternatively to, updating and storing AF episode related data, control circuit 206 may provide an AF response at block 372 by switching pacing modes. The pacemaker 14 may be operating in an atrial tracking ventricular pacing mode, e.g., VDD. In response to detecting AF, control circuit 206 may switch to a non-atrial tracking ventricular pacing mode, e.g., VDI or VVI, at block 372. In some examples, control circuit 206 may switch back to the atrial tracking pacing mode when AF is no longer being detected.

In some examples, if pacemaker 14 is configured to detect VT or VF and deliver ATP, the AF detection response provided at block 372 may include withholding ATP. Atrial depolarizations during AF may be irregularly conducted to the ventricles in some patients leading to SVT. ATP delivered to the ventricle during AF is not expected to be effective in terminating the tachyarrhythmia. Accordingly, in some examples, control circuit 206 may be configured to withhold VT detection and/or ATP therapy delivery at block 372 in response to AF being detected.

Figure 7:
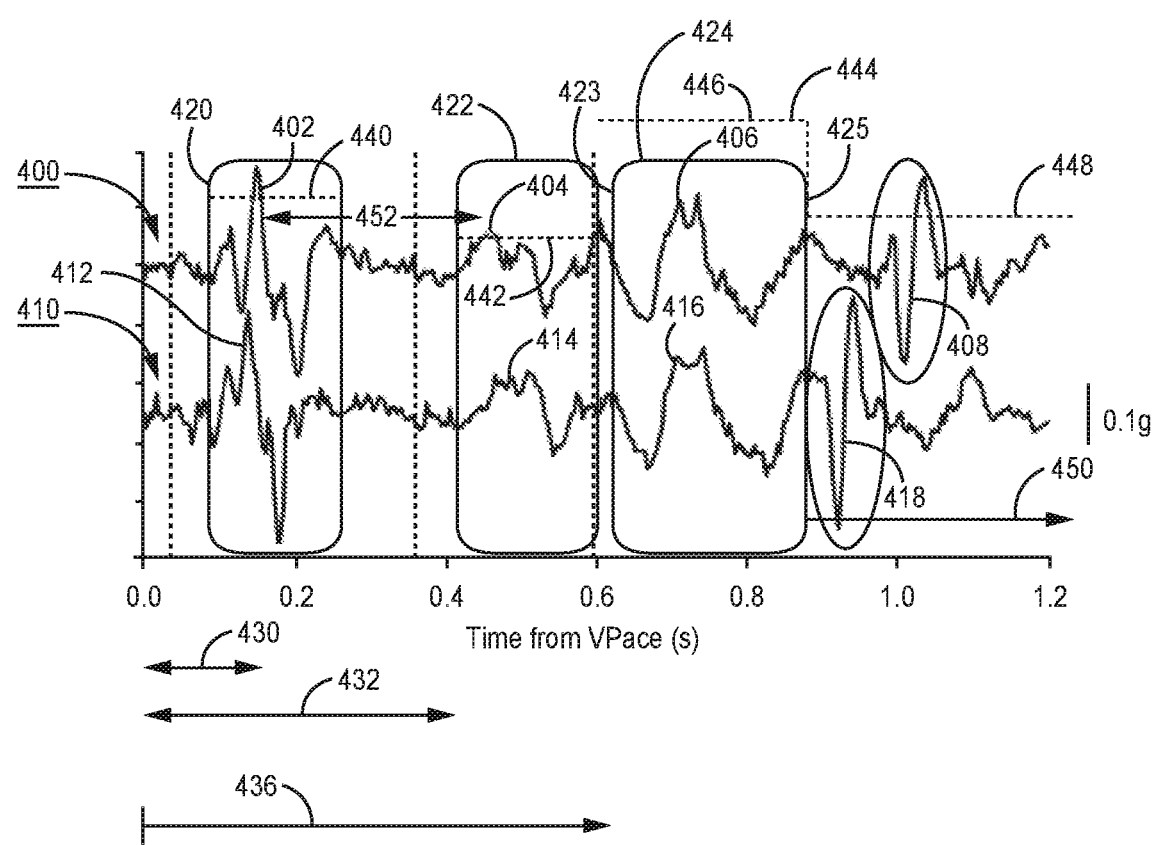
FIG. 7 depicts an example of intraventricular motion sensor signals acquired over two different cardiac cycles.

FIG. 7 is an example of motion sensor signals 400 and 410 acquired over two different cardiac cycles. A ventricular pacing pulse is delivered at time 0.0 seconds for both cardiac cycles. The top sensor signal 400 is received over one cardiac cycle, and the bottom sensor signal 410 is received over a different cardiac cycle. The two signals 400 and 410 are aligned in time at 0.0 seconds, the time of the ventricular pacing pulse delivery. While motion signals 400 and 410 and motion signal 250 of FIG. 7 are shown as raw accelerometer signals, it is recognized that control circuit 80 may receive a digitized filtered, amplified and rectified signal from motion sensor 212 for processing and analysis for sensing atrial events for use in tachyarrhythmia detection.

The A1 events 402 and 412 of the respective motion sensor signals 400 and 410, which occur during ventricular contraction, are observed to be well-aligned in time following the ventricular pacing pulse at time 0.0 seconds. Similarly, the A2 events 404 and 414 (marking the isovolumic ventricular relaxation phase and end of ventricular systole and start of ventricular diastole) and the A3 events 406 and 416 (occurring during passive ventricular filling during ventricular diastole) are well-aligned in time. Since the A1, A2 and A3 events are ventricular events, occurring during ventricular contraction, isovolumic ventricular relaxation, and passive ventricular filling, respectively, these events are expected to occur at relatively consistent intervals following a ventricular electrical event, the ventricular pacing pulse in this example. The time relationship of the A1, A2 and A3 events may be different following a ventricular pacing pulse compared to following a sensed intrinsic R-wave. During a stable paced or intrinsic ventricular rhythm, however, the relative timing of A1, A2 and A3 events to each other and the immediately preceding ventricular electrical event is expected to be relatively consistent from beat-to-beat. The time interval 452 between the A1 and A2 events may shorten, however, in the presence of AF. Shortening of the A1-A2 interval may occur during AF due to changes in heart chamber filling, resulting in earlier closure of the aortic and pulmonic valves and shortening of the systolic time interval. In some examples, the A1-A2 interval 452 may be determined by control circuit 206 for use as positive evidence of AF in detecting an atrial arrhythmia. Detection of A1-A2 interval shortening may be used by control circuit 206 for increasing the likelihood of detecting AF in the presence of VCL irregularity.

The A4 events 408 and 418 of the first and second motion sensor signals 400 and 410 respectively are not aligned in time. The A4 event occurs during atrial systole and as such the time interval of the A4 event following the immediately preceding ventricular electrical event (sensed R-wave or ventricular pacing pulse) and the preceding A1 through A3 ventricular events may vary between cardiac cycles.

The timing of the A1 through A3 events relative to each other and the immediately preceding ventricular electrical event may be used for determining an atrial blanking period 436 and increasing confidence in reliably detecting A4 events 408 and 418. The atrial systolic event is not detected during the atrial blanking period 436 which extends from the ventricular electrical event (at time 0.0) through an estimated onset of ventricular diastole so that the atrial blanking period 436 includes both the A1 and A2 events. An A3 window 424 may be set having a starting time 420 corresponding to the end of the post-ventricular atrial blanking period 436 and an ending time 425. The ending time 425 may be established based on timing of the A3 event or an expected end time of the passive ventricular filling phase after a ventricular electrical event.

A4 events 408 and 418 may be detected based on a multi-level A4 sensing threshold 444. As seen by the lower motion sensor signal 410, the A4 event 418 may occur earlier after the A3 window 424 due to changes in atrial rate. In some instances, as the atrial rate increases, the A4 event 418 may occur within the A3 window 424. When this occurs, the A3 event 416 and the A4 event 418 may fuse as passive and active ventricular filling occur together. The fused A3/A4 event may have a high amplitude, even greater than the amplitude of either the A3 event 416 or the A4 event 418 when they occur separately. As such, in some examples a first, higher A4 sensing threshold amplitude 446 may be established for detecting an early A4 signal that is fused with the A3 signal during the A3 window 424. A second, lower A4 sensing threshold amplitude 448 may be established for detecting relatively later A4 signals, after the ending time 425 of the A3 window 424. The A3 window ending time 425 may also be considered a starting time of an A4 sensing window 450, though A4 signals may be sensed during the A3 window when the higher sensing threshold amplitude 446 is crossed. The earliest crossing of the A4 sensing threshold 444 by the motion sensor signal after the starting time 420 of the A3 window (or after the expiration of the atrial blanking period 436) may be detected as the atrial systolic event.

Ventricular A1 and A2 events may be sensed during the atrial blanking period 436 by control circuit 206 for use in monitoring A1-A2 interval shortening. An A1 window 420 may be set based on an expected A1 time interval 430 between a ventricular electrical event and the A1 event 402 or 412. An A2 window 422 may be set based on an expected time interval 432 from the ventricular electrical event until the A2 event 404 or 414. The timing of the A1 window 420 and A2 window 422 may adapt to changing ventricular rate. An A1 sensing threshold 440 may be applied to the motion sensor signal during the A1 window 420, and an A2 sensing threshold 442 may be applied to the motion signal during the A2 window 422. The time interval between an A1 sensing threshold crossing and an A2 sensing threshold crossing may be determined by control circuit 206 as the A1-A2 interval 452. In other examples, a morphology waveform or feature of the A1 signal and A2 signal may be used in addition to, or alternatively to, the two respective threshold crossings during a set time window 420 or 422 for detecting the A1 and A2 events and for subsequently determining A1-A2 interval shortening.

Figure 8:
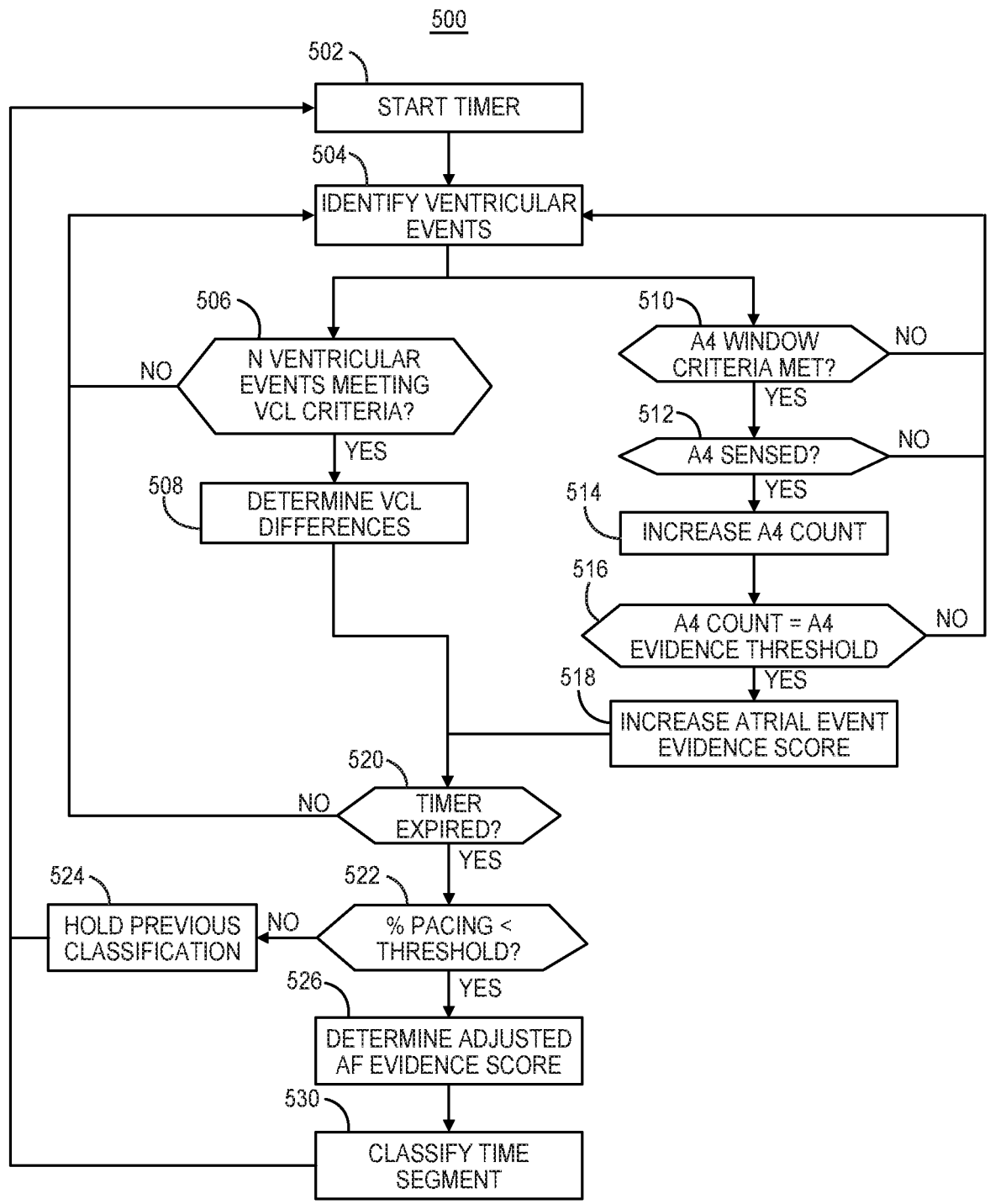
FIG. 8 is a flow chart of a method for determining an atrial arrhythmia evidence score based on a combination of atrial events sensed from a motion signal and ventricular cycle lengths.

FIG. 8 is a flow chart 500 of a method for determining an AF evidence score based on a combination of atrial events sensed from a motion signal and VCLs. An analysis of VCLs and sensed atrial events may be determined over a predetermined time interval, e.g. one minute, two minutes, or other time interval, which may be less than or greater than one minute. In one example, control circuit 206 sets a timer to two minutes at block 502. At bock 504, a ventricular event is identified. The ventricular event may be an electrical event, e.g., a sensed, intrinsic R-wave or a delivered ventricular pacing pulse. In other examples, the ventricular events may be identified as ventricular mechanical events (e.g., A1 events) sensed from the motion signal produced by motion sensor 212.

At block 506, control circuit 206 determines if a predetermined number of ventricular events (sensed R-waves, delivered ventricular pacing pulses or a combination thereof) meeting VCL criteria have been identified. For instance, four ventricular events may be required to determine two consecutive VCL differences. One VCL is determined between two consecutively identified ventricular events, e.g., "V1" and "V2." A second VCL consecutively following the first VCL is determined between the second ventricular event, "V2," and a third ventricular event, "V3." One VCL difference, AWL, can be determined between the first and second VCLs (e.g., VCL1−VCL2=ΔVCL1). Thus, determination of one VCL difference, ΔVCL1, requires three consecutively identified ventricular events, V1, V2 and V3.

In some examples, two VCL differences are determined to generate an ordered pair (ΔVCL1, ΔVCL2) that defines a point in a two-dimensional Lorenz plot area. The distribution of ordered pairs of the VCL differences may be used for determining an AF evidence score. For example, the process of determining an AF evidence score may include populating histogram bins of a two-dimensional Lorenz plot area with a count of the ordered pairs (ΔVCL1, ΔVCL2) that fall into each two-dimensional histogram bin range, e.g., as generally disclosed in the above-incorporated patents. In order to determine two consecutive VCL differences to generate one data point defined by the ordered pair (ΔVCL1, ΔVCL2), four ventricular events need to be identified at block 506. The first three ventricular events, V1, V2 and V3, define two consecutive VCLs and ΔVCL1. One more ventricular event, "V4," along with the preceding ventricular event V3 defines a third consecutive VCL. The difference between the second VCL and the third VCL is determined as the second VCL difference, ΔVCL2, for defining the ordered pair (ΔVCL1, ΔVCL2). Thus, control circuit 206 continues to identify ventricular events at block 504 until four ventricular events are identified (block 506) for determining two consecutive VCL differences at block 508.

In some examples, additional criteria are applied to the identified ventricular events and VCLs at block 506 before determining the VCL differences at block 508. For instance, a maximum number of pacing pulses, e.g., one ventricular pacing pulse out of the four identified ventricular events, may be allowed. Additionally or alternatively, each of the three VCLs defined by the four identified ventricular events may be required to be greater than a predetermined VCL threshold at block 506. According to one example, control circuit 206 determines whether each of the VCLs is greater than 220 milliseconds. The interval threshold may be an SVT limit defined to reduce the likelihood of AF detection based on VCLs shorter than the SVT limit, which may be evidence of a true fast VT or VF.

At block 508, VCL differences are determined from the N ventricular events meeting VCL criteria. If the timer has not expired, VCL differences continue to be determined for generating ordered pairs of two consecutive VCL differences for populating a two-dimensional Lorenz plot histogram. In other examples, VCLs may be accumulated and analyzed according to other VCL- or RRI-based AF detection criteria that do not necessarily collect the VCL differences in ordered pairs for populating a Lorenz plot histogram. The techniques disclosed herein that utilize A4 event sensing from a motion signal for detecting atrial beats as evidence against an AF detection may be used in combination with a variety of AF detection criteria.

Control circuit 206 may concurrently acquire atrial event sensing data during the predetermined time segment, while VCL data is being acquired. Control circuit 206 may determine if A4 signals are sensed during the predetermined time segment. The more A4 signals being sensed as one A4 event per VCL during the predetermined time segment, the less likely AF is present. As such, increasing evidence of one sensed atrial event per VCL is used to decrease the probability of AF being detected.

At block 510, control circuit 206 may apply criteria for counting an A4 sensed event. To reduce the likelihood of A4 oversensing, A4 event sensing for the purposes of tachyarrhythmia detection may be performed only during the A4 window, e.g., the time interval between the preceding A3 window ending time and the next ventricular event. During short VCLs, the A3 and A4 events may be fused making it difficult to confidently discern the A4 event or the A1 event may occur early, potentially being oversensed as A4 events during the A4 window. Accordingly, criteria may be applied at block 510 to the A4 window and/or VCL to promote reliable A4 event sensing for use in determining the atrial event evidence score.

For example, the A4 window 450 shown in FIG. 7, between the A3 window ending time 425 and the next ventricular event (identified at block 504) may be required to be greater than a threshold time interval in order to count an A4 event sensed during the A4 window toward reducing the probability of detecting AF. The A4 window may be required to be at least 400 ms as an example. If the A4 window is less than a threshold time duration, the A4 window may be ignored in determining an atrial event evidence score. In other examples, the VCL may be required to be longer than a predetermined threshold at block 510 in order for A4 event sensing during the corresponding A4 window to be used in accumulating atrial event evidence against detecting an AF rhythm. Criteria may be applied to the VCL at block 510 instead of or in addition to the A4 window. For example, the VCL ending with the ventricular event identified at block 504 may be required to be greater than a threshold VCL interval, e.g., at least 700 ms, or more. In other examples, criteria applied at block 510 may include a requirement of a minimum VCL difference between two consecutive VCLs in order to utilize A4 event sensing for AF detection. For instance, the VCL may be required to be greater than a threshold interval, e.g., 700 to 800 ms, and the VCL difference with the preceding VCL may be required to be greater than a difference threshold, e.g., 100 ms, in order for an A4 event to be counted toward reducing the probability of detecting AF. The criteria applied at block 510 may be optional, and control circuit 206 may increase the A4 count at block 514 in response to each A4 sensed event signal received from atrial event detector 240 that represents a single A4 sensing threshold crossing during a VCL.

Control circuit 206 waits for the next identified ventricular event at block 504 if the A4 interval criteria are unmet at block 510 or when an A4 event is not sensed during the A4 window at block 512. In response to an A4 event being sensed during the A4 window that meets the criteria required at block 510 ("yes" branch of block 512), control circuit 206 may increase the value of an A4 counter at block 514. In other examples, the value of the A4 counter may be increased in response to the motion signal crossing the A4 threshold 444 during the A3 window 424 or during the A4 window 450 in the current ventricular cycle.

Control circuit 206 may compare the value of the A4 counter to an A4 evidence threshold at block 516. If the A4 count value has not reached an A4 evidence threshold value ("no" branch of block 516), the process returns to block 504 to identify the next ventricular event as long as the predetermined time interval has not expired ("no" branch of block 520). If the A4 evidence threshold is reached, control circuit 206 may increase the atrial event evidence score at block 518. According to one example, the atrial event evidence score is increased by one in response to the A4 count reaching a value of 4. In other examples, the atrial event evidence score may be increased by one each time the A4 count reaches a predetermined value that may be less than or greater than four. In still other examples, the atrial event evidence score may be set equal to the A4 count so that the A4 count is used directly as the atrial event evidence score that is used to adjust the AF evidence score.

In some examples, additional analysis of the A4 sensed events may be performed before increasing the atrial event evidence score at block 518. For example, a predetermined number of sensed A4 event signals, with each being detected as one A4 signal per VCL, may be ensemble averaged. Control circuit 206 may determine one or more signal features from the ensemble averaged A4 signal and compare the signal features to criteria for confirming that the averaged signal represents true A4 signals. If the A4 signal criteria are met, control circuit 206 increases the atrial event evidence score at block 518.

After increasing the atrial event evidence score (block 518), if the timer has not expired ("no" branch of block 520), control circuit 206 returns to block 504 to identify the next ventricular event and continues to count sensed A4 events and updating the atrial event evidence score at block 518 as needed. Upon expiration of the timer at block 520, control circuit 206 may determine the percentage of identified ventricular events that were ventricular pacing pulses during the expired time segment. The percentage of ventricular pacing pulses may be determined out of all identified ventricular events or out of only the ventricular events used to determine VCLs after meeting VCL criteria at block 506.

If the percentage of ventricular events that are ventricular pacing pulses is greater than a pacing limit threshold at block 522, control circuit 206 may withhold classifying the currently expired time segment. VCL data acquired during relatively frequent ventricular pacing may be considered unreliable for detecting AF based on VCLs. If the pacing mode is an atrial-tracking ventricular pacing mode, a high frequency of pacing determined at block 522 may be indicative of a high incidence of A4 event sensing, which is a contraindication for detecting AF.

Accordingly, if the percentage of pacing pulses is greater than the threshold, e.g., greater than 30%, control circuit 206 may withhold determining an AF evidence score for the currently expired time segment. The currently expired time segment may be ignored for the purpose of detecting AF in some examples. In some examples, a predetermined number of time segments may be required to be classified as AF based on the AF evidence score in order to detect AF. In this case, the currently expired time segment may not be classified based on a new AF evidence score but may be given the same classification of the preceding time segment, held for the currently expired time segment at block 524. For instance, if the preceding time segment was classified as AF, the currently expired time segment may also be classified as AF. If the previous time segment was classified as non-AF, the currently expired time segment may also be classified as non-AF.

When the percentage of pacing pulses is less than the threshold at block 522, control circuit 206 determines the AF evidence score at block 526 based on the VCL differences determined at block 508 and adjusted by the atrial event evidence score determined at block 518. The AF evidence score may be determined based on a distribution of the ordered pairs of VCL differences in a two-dimensional Lorenz plot histogram. A high number of occupied histogram bins indicates high VCL irregularity and is evidence of AF. A high frequency of occupied histogram bins surrounding the origin of a two-dimensional Lorenz plot coordinate system indicates very low VCL irregularity, which may be evidence of normal sinus rhythm or highly organized atrial tachycardia and is not an indication of AF. In one example, the AF evidence score based on VCLs may be determined by subtracting the number of ordered pairs of VCL differences falling in histogram bins within a defined region around the origin from the total number of occupied histogram bins outside the region around the origin. In some examples, evidence of regular premature atrial contractions (PACs) may be determined from the Lorenz plot histogram based on a clustering of ordered pairs of VCL differences that is a signature pattern of PACs. Frequent PACs may occur at regular coupling intervals and present regular patterns of VCLs, e.g., associated with bigeminy (short-short-long RRIs) or trigeminy (short-short-short-long RRIs). Accordingly, the AF evidence score before adjustment by the atrial event evidence score may be determined by subtracting the count of ordered pairs within the origin region and subtracting a number of counts within predefined segments of the Lorenz plot histogram area corresponding to PAC patterns of VCLs. Various techniques for determining an AF evidence score based on VCLs or other VCL irregularity metrics, which may be performed by control circuit 206, are generally described in the above incorporated U.S. Pat. No. 7,031,765 (Ritscher et al.); U.S. Pat. No. 7,623,911 (Sarkar, et al.); U.S. Pat. No. 7,537,569 (Sarkar, et al.), and in U.S. Pat. No. 7,627,368 (Houben et al).

The AF evidence score determined based on the VCL differences may be adjusted based on the incidence of atrial event sensing. Control circuit 206 may subtract the atrial event evidence score determined at block 518 from the VCL-based AF evidence score to obtain the adjusted AF evidence score at block 526. The adjusted AF evidence score is compared to an AF threshold at block 530 for classifying the currently expired time segment, e.g., as AF or non-AF. The AF score threshold may be selected and optimized based on historical clinical data of selected patient populations or historical individual patient data, and the optimal AF score threshold setting may vary from patient to patient. In an illustrative example, the AF score may have a possible range of 0 to 100. The AF score threshold may be set between 25 and 75. If the AF score meets or crosses an AF score threshold, the time segment over which the VCLs were collected, and thus the cardiac signal occurring within that time segment, is classified as an AF time segment. One or more AF time segments may be required to detect an AF rhythm, e.g., as described in conjunction with FIG. 6.

Figure 9:
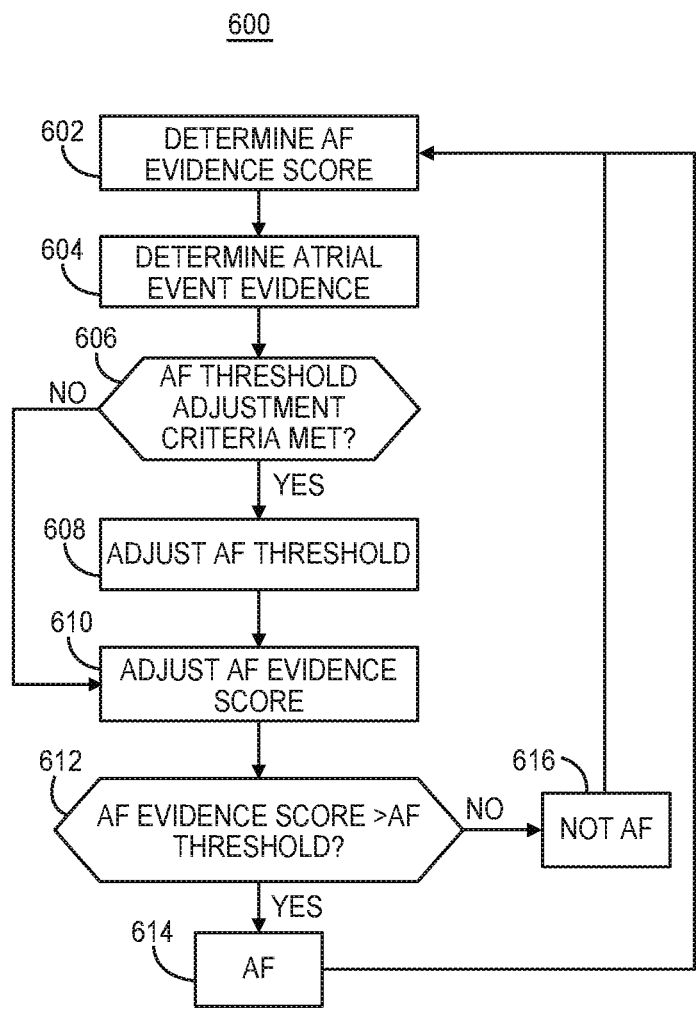
FIG. 9 is a flow chart of a method that may be performed for detecting an atrial arrhythmia according to another example.

FIG. 9 is a flow chart 600 of a method that may be performed for detecting AF according to another example. At block 602, control circuit 206 determines an AF evidence score based on VCL differences, e.g., using any of the techniques described above or in the incorporated references. At block 604, control circuit 206 determines atrial event evidence. Atrial event evidence may be determined by counting the number of sensed A4 signals, which occur as one sensed A4 signal per VCL, over the time segment that VCLs are determined for determining the AF evidence score. An atrial event evidence score may be determined based on sensed A4 signals, e.g., by increasing the atrial event evidence score by one after every four (or other predetermined number of) A4 sensed event signals.

Control circuit 206 may determine if AF threshold adjustment criteria are met at block 606. Control circuit 206 may compare the number of atrial events sensed (one per VCL) over the time segment that the VCLs were acquired to a threshold number at block 606. The number of sensed A4 signals, or an atrial event evidence score based on the number of sensed A4 signals, may be compared to the threshold. For example, if no more than one A4 event is sensed during a two-minute time segment, the AF threshold may be adjusted, e.g., lowered, at block 608 to increase the likelihood of classifying the heart rhythm during the predetermined time segment as being AF and ultimately detecting AF. In other examples, another maximum predetermined number of sensed A4 events, as low as zero A4 events, may be defined as criteria for adjusting the AF threshold in a manner that increases the likelihood of detecting AF. Very few or no A4 events sensed during the VCLs used to determine the AF evidence score is positive evidence for AF.

The percentage of pacing during the time segment over which the AF evidence score is determined may also be taken into account when determining if criteria for adjusting the AF detection threshold are met. For instance, if 20 to 40% of the ventricular events identified for determining VCL differences are pacing pulses, and less than a maximum threshold number of A4 events are sensed, the AF detection threshold may be decreased at block 608. The presence of a relatively high percentage of paced ventricular cycles, e.g., greater than 40%, will reduce the AF evidence score since the VCLs will be less irregular during frequent ventricular pacing. To account for this reduced irregularity of VCL, the AF detection threshold may be decreased when there are very few (or no) A4 events sensed during relatively frequent pacing to still allow detection of AF during pacing. Accordingly, criteria defined at block 606 may define one or more ranges of pacing percentages and a corresponding maximum threshold number of sensed A4 events as criteria for adjusting the AF threshold by a respective predetermined amount.

During atrial tachycardia or atrial flutter, an atrial beat may occur more than once during the A4 window. In some examples, multiple peaks or A4 threshold amplitude crossings during the A4 window may be evidence of an atrial tachyarrhythmia that is not AF. As such, atrial event evidence determination at block 604 may include determining the number of peaks during an A4 window or determining a number of A4 sensing threshold crossings during an A4 window. When multiple peaks or multiple A4 sensing threshold crossings occur within a single A4 window, during one or more VCLs, criteria for reducing the AF threshold is not met at block 606. The AF threshold may remain the same or even be increased to reduce the likelihood of detecting AF when multiple A4 sensing threshold crossings or motion signal peaks occur within a single A4 window.

At block 610, control circuit 206 may adjust the VCL-based AF evidence score by subtracting an atrial event evidence score as described above in conjunction with FIG. 8. The adjusted AF evidence score is compared to the AF detection threshold at block 612, which may be the adjusted AF detection threshold if criteria are met at block 606. In some examples, the AF detection threshold may be adjusted based on an absence of sensed A4 signals with or without adjusting the AF evidence score based on atrial event evidence.

If the AF evidence score is greater than the AF threshold at block 612, the cardiac rhythm during the time segment over which the AF evidence score was determined is classified as AF at block 614. An AF detection and AF detection response may be made as described in conjunction with FIG. 6. The time segment is not classified as AF at block 616 if the adjusted AF evidence score is not greater than the AF threshold. The process may return to block 602 to determine an AF evidence score for the next time segment.

In some examples, when control circuit 206 determines that multiple A4 sensing threshold crossings occur within a single VCL, for one or more VCLs, at block 604 when determining atrial event evidence, the control circuit 206 may detect the atrial tachyarrhythmia as being atrial flutter at block 614 rather than AF. Additional analysis may be performed at block 604 to determine if the morphology of the multiple A4 sensing threshold crossing waveforms are similar and thus represent a series of atrial flutter events. If the morphology is varying, the classification at block 614 may be AF. More generally, multiple A4 sensing threshold crossings within a single VCL may be evidence of atrial tachyarrhythmia, and the classification made at block 614 may be atrial tachyarrhythmia without discrimination between atrial flutter and AF.

As shown by the flow chart of FIG. 9, an analysis of the number of A4 events sensed during a time segment over which VCLs are determined may be used to adjust the VCL-based AF evidence score, an AF threshold applied to the AF evidence score, or both. A low incidence or absence of sensed A4 events, or multiple A4 sensing threshold crossings per VCL, may increase the likelihood of detecting atrial tachycardia when VCLs are irregular due to a decreased AF threshold and/or little or no adjustment of the VCL-based AF evidence score. A relatively higher incidence of A4 events sensed once per VCL decreases the likelihood of detecting AF due to a non-adjusted or increased AF threshold and/or a decreased AF evidence score after adjusting by the atrial event evidence.

Figure 10:
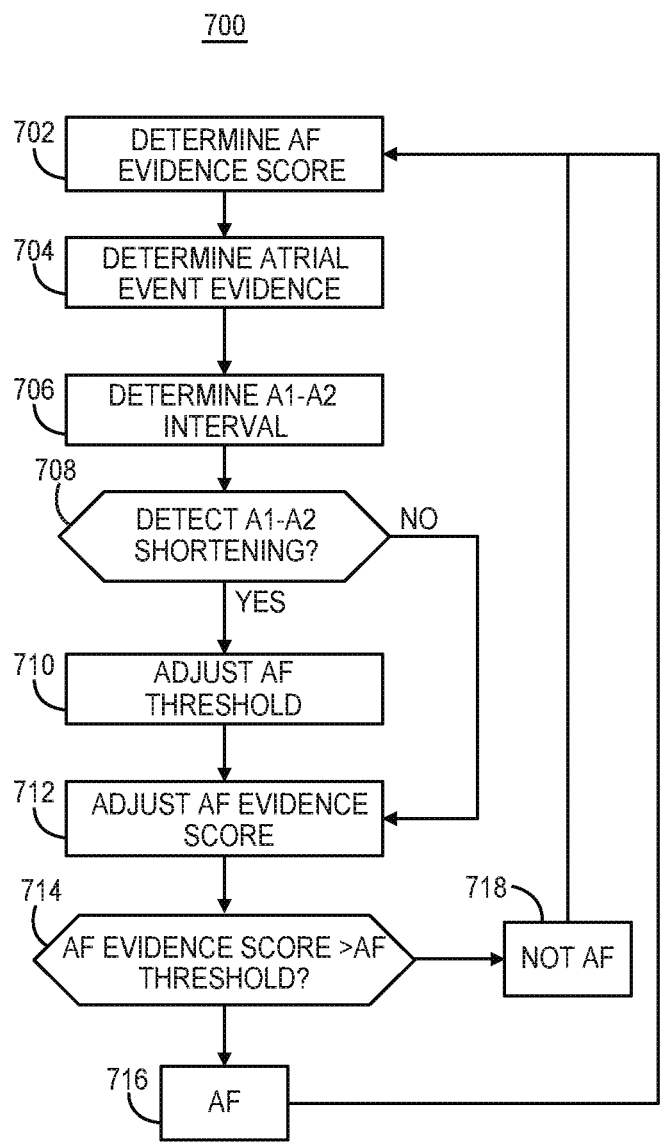
FIG. 10 is a flow chart of a method for detecting an atrial arrhythmia using an intraventricular motion sensor signal and VCLs according to another example.

FIG. 10 is a flow chart 700 of a method for detecting AF using a motion sensor signal and VCLs according to another example. After determining the VCL-based AF evidence score at block 702, control circuit 206 may determine atrial event evidence from the motion signal at block 704, e.g., by counting sensed A4 events as described above. In this example, shortening of the A1-A2 interval may be determined from the motion sensor signal as positive evidence for AF. At block 706, the A1 and A2 events are detected from the motion signal by control circuit 206. The A1 and A2 events may be sensed based on threshold crossings of the motion signal after an identified ventricular electrical event, e.g., during A1 and A2 windows as shown in FIG. 7, which may be heart rate-adaptive windows. Control circuit 206 may determine the time interval between the sensed A1 and A2 events. A1-A2 intervals may be determined during each one of multiple VCLs during the predetermined time segment. In other examples, the A1-A2 interval may be determined at the beginning, at the end or during VCLs selected according to a sampling rate during the AF evidence score time segment over which VCLs are collected. Multiple A1-A2 intervals determined during different VCLs may be averaged to determine a representative A1-A2 interval during the time segment. In some examples, the A1-A2 interval is determined during a VCL in which no A4 event is sensed or during the VCL immediately following a VCL in which no A4 event is sensed.

Shortening of the A1-A2 interval may be a positive indicator of AF and used to adjust the AF threshold at block 708. For instance, the AF threshold that is compared to the AF evidence score may be decreased in response to detecting A1-A2 shortening to increase the likelihood of detecting AF during periods of irregular VCLs. Control circuit 206 may detect A1-A2 interval shortening by comparing an A1-A2 interval determined over the time period that VCLs are collected to an A1-A2 interval determined previously, e.g., during a time segment having low VCL irregularity (or low AF evidence score). A period of low VCL irregularity may be identified as a time segment in which the number of occupied bins in a Lorenz plot histogram is less than a predetermined threshold. During normal sinus rhythm, the number of (ΔVCL1, ΔVCL2) points in histogram bins around the origin of a Lorenz plot is high so that the number of occupied bins outside the origin segment less the number of (ΔVCL1, ΔVCL2) points within the origin segment is a low value, e.g., zero or even negative. As such, a period of low VCL irregularity may be identified when the AF evidence score is zero or less. A normal or baseline A1-A2 interval may be determined during this period of low VCL irregularity for comparison to an A1-A2 interval during an unknown rhythm. Any time period having a low number of occupied bins outside the origin segment, a high number of (ΔVCL1, ΔVCL2) points in the origin segment or generally a low, non-adjusted AF evidence score may be identified as a period of low VCL variability during which a normal or baseline A1-A2 interval may be determined.

A1-A2 shortening may be detected at block 706 in response to a threshold decrease in the A1-A2 interval compared to a previously determined A1-A2 interval. For example, if the A1-A2 interval determined at block 706 is at least 20% shorter than an A1-A2 interval determined during a period of low VCL irregularity (e.g., during a known non-tachyarrhythmia rhythm), A1-A2 interval shortening may be detected. In other examples, the A1-A2 interval determined at block 706 may be compared to a threshold A1-A2 interval stored in memory 210. In response to detecting A1-A2 interval shortening ("yes" branch of block 706), the AF threshold is adjusted at block 708. The AF threshold may be decreased in order to increase the likelihood of detecting AF based on the AF evidence score determined from the VCLs. The AF threshold may be decreased by a predetermined decrement or percentage, e.g., 20%, 30% or other value.

When A1-A2 interval shortening is not detected, the process may advance from block 706 to block 710 without adjusting the AF threshold. In other examples, the AF threshold may be adjusted at block 708 based on the atrial event evidence determined at block 704, e.g., as described above in conjunction with FIG. 9, even though A1-A2 interval shortening is not detected. As such, the AF threshold may be decreased at block 708 based on the absence (or very low count) of sensed A4 events during the time segment and/or based on detecting A1-A2 interval shortening. In various examples, the AF threshold may be decreased in response to either an absence of A4 sensed events or A1-A2 interval shortening; decreased only if both A1-A2 interval shortening is detected and A4 events are not sensed; or decreased by a first adjustment based on an absence or low incidence of A4 events sensed once per VCL and decreased by a second adjustment in response to A1-A2 interval shortening.

After adjusting the AF threshold as needed at block 708, the AF evidence score may be adjusted based on the detection of A1-A2 interval shortening in addition to or instead of adjusting the AF threshold. For instance, the AF evidence score may be increased in response to detecting A1-A2 interval shortening. The increase may be a predetermined increment or percentage of the AF evidence score, making it more likely that AF is detected during a period of VCL irregularity. The AF evidence score may additionally or alternatively be adjusted based on the atrial event evidence as described above.

At block 712, the AF evidence score is compared to the AF threshold, after adjusting one or both as needed based on atrial event evidence and/or A1-A2 interval shortening detection. If the AF evidence score is greater than the AF threshold, the cardiac rhythm during the AF evidence score time segment (over which the VCLs were acquired) is classified as AF at block 714. If not, the cardiac rhythm is not classified as AF at block 716. The process may return to block 702 to determine the next AF evidence score over the next time segment.

Figure 11:
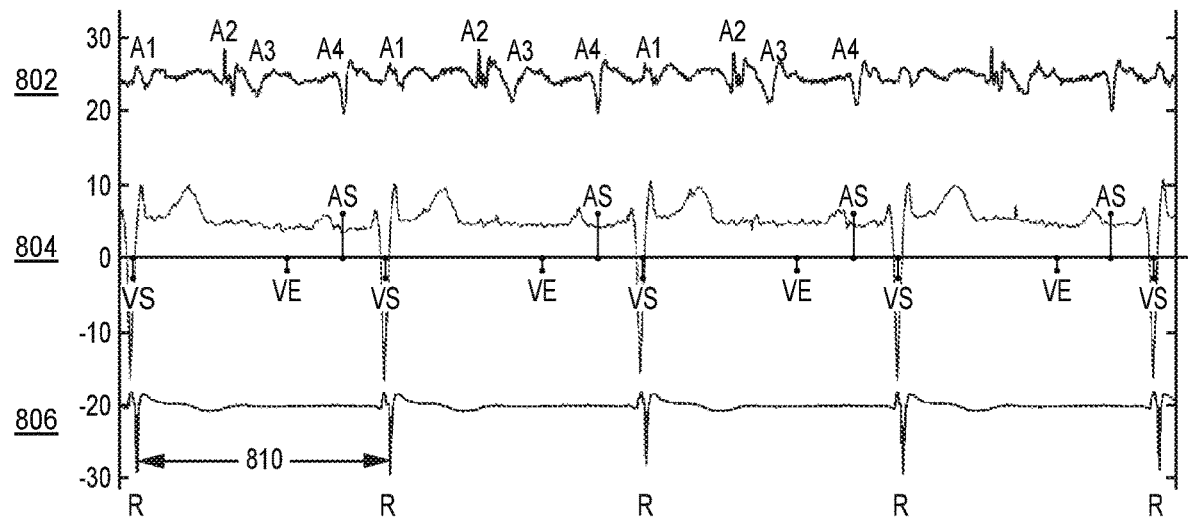
FIG. 11 is a graph of an example accelerometer signal, electrocardiogram (ECG) signal with event markers and ventricular electrogram (EGM) signal during a non-atrial tracking pacing mode with normal AV conduction intact.

FIG. 11 is a graph of example an accelerometer signal 802, ECG signal 804 with event markers and ventricular EGM signal 806 during a non-atrial tracking pacing mode with normal AV conduction intact. The accelerometer signal 802 is an example of a motion signal that is received by the control circuit 206 from the motion sensor 212 (shown in FIG. 3). Accelerometer signal 802 is shown as a non-rectified signal in FIG. 11 but may be rectified by motion sensor 212 or control circuit 206 for sensing A4 events. The A1, A2, A3 and A4 events are denoted along the motion signal 802.

The "VE" markers shown along ECG signal 804 indicate the end of the A3 window, e.g., corresponding to ending time 425 shown in FIG. 7. The "AS" markers indicate the time of an A4 sensed event, e.g., when the A4 signals of accelerometer signal 802 cross the A4 sensing threshold. The "VS" markers indicate an R-wave sensed event. R-waves (labeled "R") of EGM signal 806 are sensed by sensing circuit 204, which passes an R-wave sensed event signal to control circuit 206. In this example, one A4 signal is being sensed per VCL (each RR interval 810). The occurrence of one A4 signal sensed per VCL is evidence against atrial tachyarrhythmia. In this example VCLs (determined as RR intervals 810) are not irregular, so the AF evidence score would be very low or even negative.

Figure 12:
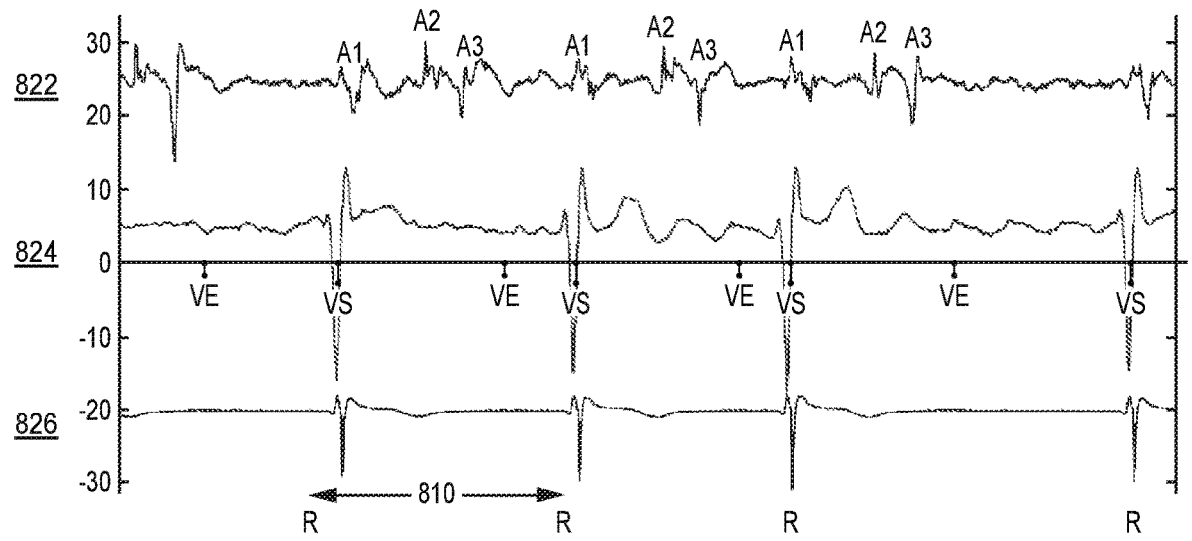
FIG. 12 is a graph of an example accelerometer signal, ECG signal with event markers, and ventricular EGM signal during atrial fibrillation.

FIG. 12 is a graph of an example accelerometer signal 822, ECG signal 824 with event markers, and ventricular EGM signal 826 during atrial fibrillation. No clear A4 signals are observed on the accelerometer signal 822. Following each ending time (VE) of the A3 window, no AS marker is present indicating that no A4 events are being detected. The VS markers indicate the time of R-wave sensed events, corresponding to R-waves of the EGM signal 826. The RR intervals 810 in this example are observed to be irregular. This irregularity is likely to lead to a relatively high AF evidence score. The absence of A4 events results in an atrial event evidence score of zero, such that no adjustments to the AF evidence score (or AF threshold) is made. AF is likely to be properly detected based on the VCL irregularity and the absence of any A4 event sensing from the motion signal.

Various examples of a medical device and method for detecting an atrial tachyarrhythmia using an intra-ventricular motion signal have been described. It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. An implantable medical device, comprising:
a sensor configured to produce an intraventricular signal that includes an atrial mechanical event signal attendant to atrial mechanical systole;
a sensing circuit configured to sense ventricular events;
a memory configured to store atrial arrhythmia episode data;
and a control circuit coupled to the sensor, the sensing circuit, and the memory, the control circuit configured to:
determine a first atrial arrhythmia score from the ventricular events sensed by the sensing circuit, the first atrial arrhythmia score correlated to a presence of atrial arrhythmia;
determine a second atrial arrhythmia score from the intraventricular signal based on the atrial mechanical event signals by:
identifying a plurality of ventricular events;
starting an atrial event window following each one of the ventricular events;
determining an atrial event window duration from the start of the atrial event window until a next one of the plurality of ventricular events;
in response to the atrial event window duration being less than a threshold window duration, ignore the atrial event window in determining the second atrial arrhythmia score;
determining a count of atrial mechanical event signals that are sensed from the intraventricular signal during the atrial event windows that are at least the threshold window duration; and
determining the second atrial arrhythmia score based on the count of sensed atrial mechanical event signals;
detect an atrial arrhythmia based on the first atrial arrhythmia score and the second atrial arrhythmia score; and
update the atrial arrhythmia episode data stored in the memory in response to detecting the atrial arrhythmia, the update including an indication of the detected atrial arrhythmia.

2. The pacemaker of claim 1, wherein the control circuit is further configured to detect the atrial arrhythmia by:
adjusting the first atrial arrhythmia score based on the second atrial arrhythmia score;
comparing the adjusted first atrial arrhythmia score to an arrhythmia threshold; and
detecting the atrial arrhythmia in response to the adjusted first atrial arrhythmia score being greater than the arrhythmia threshold.

3. The device of claim 2, wherein the control circuit is further configured to adjust the arrhythmia threshold in response to the second atrial arrhythmia score being less than an adjustment threshold.

4. The device of claim 2, wherein the control circuit is further configured to:
detect a plurality of atrial mechanical events from the intraventricular signal during an atrial event window; and
adjust at least one of the first atrial arrhythmia score and the arrhythmia threshold in response to detecting the plurality of atrial mechanical events during the atrial event window.

5. The device of claim 1, wherein the control circuit is further configured to:
detect a plurality of atrial mechanical events from the intraventricular signal during an atrial event window; and
detect atrial flutter in response to detecting the plurality of atrial mechanical events.

6. The device of claim 1, wherein the control circuit is configured to detect the atrial arrhythmia by:
comparing the first atrial arrhythmia score to a first threshold;
comparing the second atrial arrhythmia score to a second threshold; and
detecting the atrial arrhythmia in response to the first atrial arrhythmia score being greater than the first threshold and the second atrial arrhythmia score being less than the second threshold.

7. The device of claim 1, wherein the sensor comprises a motion sensor configured to produce an intraventricular motion signal comprising the atrial mechanical event signal.

8. The device of claim 1, wherein the sensor comprises one of an impedance sensor configured to produce an intraventricular impedance signal and a pressure sensor configured to produce an intraventricular pressure signal;
wherein the control circuit is configured to determine the second atrial arrhythmia score by sensing atrial systolic events from one of the intraventricular impedance sensor and the intraventricular pressure sensor.

9. The device of claim 1, wherein:
the sensing circuit is configured to sense R-waves from a cardiac electrical signal; and
the control circuit is configured to:
identify the plurality of ventricular events comprising the R-waves sensed by the sensing circuit;
determine the first atrial arrhythmia score by determining a plurality of ventricular cycle lengths between consecutive pairs of the plurality of ventricular events; and
determine the second atrial arrhythmia score from the intraventricular signal during a time segment comprising the plurality of ventricular cycle lengths.

10. The device of claim 1, further comprising a pulse generator configured to deliver ventricular pacing pulses;
wherein the control circuit is further configured to:
identify a plurality of ventricular events comprising the ventricular pacing pulses delivered by the pulse generator;
determine a percentage of the plurality of ventricular events that are ventricular pacing pulses; and
withhold the atrial arrhythmia detection in response to the percentage being greater than a threshold percentage.

11. The device of claim 1, wherein the control circuit is further configured to:
detect shortening of a ventricular systolic time interval from the intraventricular signal;
adjust an arrhythmia threshold in response to detecting the shortening;
adjust the first atrial arrhythmia score based on the second atrial arrhythmia score; and
detect the atrial arrhythmia in response to the adjusted first atrial arrhythmia score being greater than the adjusted arrhythmia threshold.

12. The device of claim 1, further comprising a pulse generator configured to deliver ventricular pacing pulses;
    wherein the control circuit is configured to:
        determine the first atrial arrhythmia score by identifying a plurality of ventricular events comprising the delivered ventricular pacing pulses and determining ventricular cycle length differences from the plurality of ventricular events;
        determine the count of atrial mechanical event signals by further determining a count of ventricular cycles of the plurality of ventricular events during which a single atrial mechanical event signal is sensed from the intraventricular signal;
        determine a percentage of the identified plurality of ventricular events that are ventricular pacing pulses;
        decrease an atrial arrhythmia detection threshold in response to the second atrial arrhythmia score being less than an atrial event threshold and the percentage of the identified plurality of ventricular events that are ventricular pacing pulses being greater than a pacing frequency threshold; and
        detect the atrial arrhythmia in response to the first atrial arrhythmia score being greater than the decreased atrial arrhythmia detection threshold.

13. The device of claim 1, further comprising a pulse generator configured to:
    generate ventricular pacing pulses according to a first pacing mode; and
    in response to the control circuit detecting the atrial arrhythmia, generate the ventricular pacing pulses according to a second pacing mode different than the first pacing mode.

14. The device of claim 1, further comprising a pulse generator configured to deliver anti-tachycardia pacing therapy;
    wherein the control circuit is further configured to control the pulse generator to withhold the anti-tachycardia pacing therapy in response to detecting the atrial arrhythmia.

15. The device of claim 1, further comprising a telemetry circuit configured to transmit the atrial arrhythmia episode data in response to the updating.

16. A method, comprising:
    determining a first atrial arrhythmia score from ventricular events sensed by a sensing circuit of an implantable medical device, the first atrial arrhythmia score correlated to a presence of atrial arrhythmia;
    determining a second atrial arrhythmia score from an intraventricular signal produced by a sensor of the implantable medical device, the intraventricular signal comprising an atrial mechanical event signal attendant to atrial systole, wherein determining the second atrial arrhythmia score comprises:
        identifying a plurality of ventricular events;
        starting an atrial event window following each one of the ventricular events;
        determining an atrial event window duration from the start of the atrial event window until a next one of the plurality of ventricular events;
        in response to the atrial event window duration being less than a threshold window duration, ignoring the atrial event window in determining the second atrial arrhythmia score;
        determining a count of atrial mechanical event signals that are sensed from the intraventricular signal during the atrial event windows that are at least the threshold window duration; and
        determining the second atrial arrhythmia score based on the count of sensed atrial mechanical event signals;
    detecting an atrial arrhythmia based on the first atrial arrhythmia score and the second atrial arrhythmia score;
    updating atrial arrhythmia episode data stored in a memory of the implantable medical device in response to detecting the atrial arrhythmia, the update including an indication of the detected atrial arrhythmia.

17. The method of claim 16, wherein detecting the atrial arrhythmia comprises:
    adjusting the first atrial arrhythmia score based on the second atrial arrhythmia score;
    comparing the adjusted first atrial arrhythmia score to an arrhythmia threshold;
    detecting the atrial arrhythmia in response to the adjusted first atrial arrhythmia score being greater than the arrhythmia threshold.

18. The method of claim 17, wherein the control circuit is further configured to adjust the arrhythmia threshold in response to the second atrial arrhythmia score being less than an adjustment threshold.

19. The method of claim 17, further comprising:
    detecting a plurality of atrial mechanical events from the intraventricular signal during an atrial event window; and
    adjusting at least one of the first atrial arrhythmia score and the arrhythmia threshold in response to detecting the plurality of atrial mechanical events during the atrial event window.

20. The method of claim 16, further comprising:
    detecting a plurality of atrial mechanical events from the intraventricular signal during an atrial event window; and
    detecting atrial flutter in response to detecting the plurality of atrial mechanical events.

21. The method of claim 16, wherein detecting the atrial arrhythmia comprises:
    comparing the first atrial arrhythmia score to a first threshold;
    comparing the second atrial arrhythmia score to a second threshold; and
    detecting the atrial arrhythmia in response to the first atrial arrhythmia score being greater than the first threshold and the second atrial arrhythmia score being less than the second threshold.

22. The method of claim 16, wherein determining the second atrial arrhythmia score comprises sensing the atrial mechanical event signals from an intraventricular motion signal produced by a motion sensor of the sensor.

23. The method of claim 16, wherein determining the second atrial arrhythmia score comprises sensing atrial mechanical events from one of an intraventricular impedance signal produced by the sensor and an intraventricular pressure signal produced by the sensor.

24. The method of claim 16, further comprising:
    sensing R-waves from a cardiac electrical signal received by the sensing circuit;
    identifying the plurality of ventricular events comprising the R-waves sensed by the sensing circuit from the cardiac electrical signal;
    determining the first atrial arrhythmia score by determining a plurality of ventricular cycle lengths between consecutive pairs of the plurality of ventricular events; and determining the second atrial arrhythmia score from the intraventricular signal during a time segment comprising the plurality of ventricular cycle lengths.

25. The method of claim 16, further comprising:
identifying a plurality of ventricular events comprising ventricular pacing pulse pulses delivered by a pulse generator of the implantable medical device;
determining a percentage of the plurality of ventricular events that are ventricular pacing pulses; and
withholding the atrial arrhythmia detection in response to the percentage being greater than a threshold percentage.

26. The method of claim 16, further comprising:
detecting shortening of a ventricular systolic time interval from the intraventricular signal;
adjusting an arrhythmia threshold in response to detecting the shortening;
adjusting the first atrial arrhythmia score based on the second atrial arrhythmia score; and
detecting the atrial arrhythmia in response to the adjusted first atrial arrhythmia score being greater than the adjusted arrhythmia threshold.

27. The method of claim 16, further comprising:
determining the first atrial arrhythmia score by identifying a plurality of ventricular events comprising ventricular pacing pulses delivered by a pulse generator of the implantable medical device and determining ventricular cycle length differences from the plurality of ventricular events;
determining the count of atrial mechanical event signals by further determining a count of ventricular cycles of the plurality of ventricular events during which a single atrial mechanical event signal is sensed from the intraventricular signal;
determining a percentage of the identified plurality of ventricular events that are ventricular pacing pulses;
decreasing an atrial arrhythmia detection threshold in response to the second atrial arrhythmia score being less than an atrial event threshold and the percentage of the identified plurality of ventricular events that are ventricular pacing pulses being greater than a pacing frequency threshold; and
detect the atrial arrhythmia in response to the first atrial arrhythmia score being greater than the decreased atrial arrhythmia detection threshold.

28. The method of claim 16, further comprising:
generating ventricular pacing pulses by a pulse generator of the implantable medical device according to a first pacing mode; and
in response to detecting the atrial arrhythmia switch to generating the ventricular pacing pulses by the pulse generator according to a second pacing mode different than the first pacing mode.

29. The method of claim 16, further comprising controlling a pulse generator of the implantable medical device to withhold an anti-tachycardia pacing therapy in response to detecting the atrial arrhythmia.

30. The method of claim 16, further comprising transmitting the atrial arrhythmia episode data by a telemetry circuit of the implantable medical device.

31. A non-transitory, computer-readable storage medium comprising a set of instructions which, when executed by a control circuit of an implantable medical device, cause the device to:
determine a first atrial arrhythmia score from ventricular events sensed by a sensing circuit of the implantable medical device, the first atrial arrhythmia score correlated to a presence of atrial arrhythmia;
determine a second atrial arrhythmia score from an intraventricular signal produced by a sensor of the implantable medical device, the intraventricular signal comprising an atrial mechanical event signal attendant to atrial systole, the second atrial arrhythmia score being determined by:
identifying a plurality of ventricular events;
starting an atrial event window following each one of the ventricular events;
determining an atrial event window duration from the start of the atrial event window until a next one of the plurality of ventricular events;
in response to the atrial event window duration being less than a threshold window duration, ignoring the atrial event window in determining the second atrial arrhythmia score;
determining a count of atrial mechanical event signals that are sensed from the intraventricular signal during the atrial event windows that are at least the threshold window duration; and
determining the second atrial arrhythmia score based on the count of sensed atrial mechanical event signals;
detect an atrial arrhythmia based on the first atrial arrhythmia score and the second atrial arrhythmia score;
update atrial arrhythmia episode data stored in a memory of the implantable medical device in response to detecting the atrial arrhythmia, the update including an indication of the detected atrial arrhythmia.

32. An implantable medical device, comprising:
a sensor configured to produce an intraventricular signal that includes an atrial mechanical event signal attendant to atrial mechanical systole;
a sensing circuit configured to sense ventricular events;
a memory configured to store atrial arrhythmia episode data; and
a control circuit coupled to the sensor, the sensing circuit, and the memory, the control circuit configured to:
determine a first atrial arrhythmia score from the ventricular events sensed by the sensing circuit, the first atrial arrhythmia score correlated to a presence of atrial arrhythmia;
determine a second atrial arrhythmia score from the intraventricular signal based on the atrial mechanical event signals, wherein the control circuit is configured to determine the second atrial arrhythmia score from the intraventricular signal by:
sensing a systolic ventricular event signal from the intraventricular signal;
sensing a diastolic ventricular event signal from the intraventricular signal;
determining a ventricular systolic time interval extending from the systolic ventricular event signal to the diastolic ventricular event signal;
comparing the ventricular systolic time interval to a shortening threshold;
detecting ventricular systolic shortening based on the comparison of the ventricular systolic time interval to the shortening threshold; and
increasing the second atrial arrhythmia score in response to detecting the ventricular systolic shortening;
detect an atrial arrhythmia based on the first atrial arrhythmia score and the second atrial arrhythmia score; and update the atrial arrhythmia episode data stored in the memory in response to detecting the atrial arrhythmia, the update including an indication of the detected atrial arrhythmia.

33. A method, comprising:

determining a first atrial arrhythmia score from ventricular events sensed by a sensing circuit of an implantable medical device, the first atrial arrhythmia score correlated to a presence of atrial arrhythmia;

determining a second atrial arrhythmia score from an intraventricular signal produced by a sensor of the implantable medical device, the intraventricular signal comprising an atrial mechanical event signal attendant to atrial systole, the second atrial arrhythmia score based on the atrial mechanical event signals; wherein determining the second atrial arrhythmia score from the intraventricular signal comprises:

sensing a systolic ventricular event signal from the intraventricular signal;

sensing a diastolic ventricular event signal from the intraventricular signal;

determining a ventricular systolic time interval extending from the systolic ventricular event signal to the diastolic ventricular event signal;

comparing the ventricular systolic time interval to a shortening threshold;

detecting ventricular systolic shortening based on the comparison of the ventricular systolic time interval to the shortening threshold; and increasing the second atrial arrhythmia score in response to detecting the ventricular systolic shortening;

detecting an atrial arrhythmia based on the first atrial arrhythmia score and the second atrial arrhythmia score;

updating atrial arrhythmia episode data stored in a memory of the implantable medical device in response to detecting the atrial arrhythmia, the update including an indication of the detected atrial arrhythmia.

* * * * *

UNITED STATES PATENT AND TRADEMARK OFFICE
CERTIFICATE OF CORRECTION

| | |
|---|---|
| PATENT NO. | : 11,123,005 B2 |
| APPLICATION NO. | : 16/186937 |
| DATED | : September 21, 2021 |
| INVENTOR(S) | : Sarkar et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 152 days.

Signed and Sealed this
Fourteenth Day of February, 2023

Katherine Kelly Vidal
*Director of the United States Patent and Trademark Office*